(12) United States Patent
DeLapp et al.

(10) Patent No.: US 8,149,526 B2
(45) Date of Patent: Apr. 3, 2012

(54) SINGLE USE LENS ASSEMBLY

(75) Inventors: Scott DeLapp, San Diego, CA (US);
Theodore B. Hill, San Diego, CA (US);
Rick Sorich, Encinitas, CA (US); Scott Bradley, San Marcos, CA (US)

(73) Assignee: PhotoThera, Inc., Carlsbad, CA (US)

( * ) Notice: Subject to any disclaimer, the term of this patent is extended or adjusted under 35 U.S.C. 154(b) by 2 days.

(21) Appl. No.: 12/938,146

(22) Filed: Nov. 2, 2010

(65) Prior Publication Data

US 2011/0102916 A1  May 5, 2011

Related U.S. Application Data

(63) Continuation of application No. 12/233,498, filed on Sep. 18, 2008, now Pat. No. 7,848,035.

(51) Int. Cl.
*G02B 7/02* (2006.01)
*G02B 7/00* (2006.01)

(52) U.S. Cl. ........................ 359/820; 359/892

(58) Field of Classification Search .......... 359/694–700, 359/819–823, 892
See application file for complete search history.

(56) References Cited

U.S. PATENT DOCUMENTS

| | | | |
|---|---|---|---|
| 1,856,969 A | 5/1932 | Reiter et al. | |
| 3,735,755 A | 5/1973 | Eggleton et al. | |
| 3,810,367 A | 5/1974 | Peterson | |
| 4,076,393 A * | 2/1978 | Bates | 359/892 |
| 4,315,514 A | 2/1982 | Drewes et al. | |
| 4,343,301 A | 8/1982 | Indech | |
| 4,535,784 A | 8/1985 | Rohlicek et al. | |
| 4,539,987 A | 9/1985 | Nath et al. | |
| 4,630,273 A | 12/1986 | Inoue et al. | |
| 4,633,872 A | 1/1987 | Chaffee et al. | |
| 4,669,466 A | 6/1987 | L'Esperance | |
| 4,671,285 A | 6/1987 | Walker | |
| 4,686,986 A | 8/1987 | Fenyo et al. | |
| 4,798,215 A | 1/1989 | Turner | |
| 4,836,203 A | 6/1989 | Muller et al. | |

(Continued)

FOREIGN PATENT DOCUMENTS

DE  320 0584 A1  7/1983

(Continued)

OTHER PUBLICATIONS

U.S. Appl. No. 10/448,262, filed May 29, 2003, Oron et al.

(Continued)

*Primary Examiner* — Mohammed Hasan
(74) *Attorney, Agent, or Firm* — Knobbe, Martens, Olson & Bear LLP

(57) ABSTRACT

An optical assembly includes an output optical element having a thermally conductive and optically transmissive material and a thermal conduit in thermal communication with the output optical element and having at least one surface configured to be in thermal communication with at least one heat dissipating surface of a light delivery apparatus. The optical assembly further includes a coupling portion configured to be placed in at least two states. In a first state, the coupling portion is attached to the apparatus such that the at least one surface of the thermal conduit is in thermal communication with the at least one heat dissipating surface. In a second state, the coupling portion is detached from the apparatus after having been attached to the apparatus in the first state and in which the coupling portion is configured to prevent re-attachment of the coupling portion to the apparatus.

16 Claims, 17 Drawing Sheets

U.S. PATENT DOCUMENTS

| | | | |
|---|---|---|---|
| 4,846,196 A | 7/1989 | Wiksell et al. | |
| 4,850,351 A | 7/1989 | Herman et al. | |
| 4,930,504 A | 6/1990 | Diamantopoulos et al. | |
| 4,951,482 A | 8/1990 | Gilbert | |
| 4,951,653 A | 8/1990 | Fry et al. | |
| 4,966,144 A | 10/1990 | Rochkind et al. | |
| 4,998,930 A | 3/1991 | Lundahl | |
| 5,029,581 A | 7/1991 | Kaga et al. | |
| 5,037,374 A | 8/1991 | Carol | |
| 5,047,006 A | 9/1991 | Brandston et al. | |
| 5,054,470 A | 10/1991 | Fry et al. | |
| 5,125,925 A | 6/1992 | Lundahl | |
| 5,150,704 A | 9/1992 | Tatebayashi et al. | |
| 5,259,380 A | 11/1993 | Mendes et al. | |
| 5,265,598 A | 11/1993 | Searfoss et al. | |
| 5,267,294 A | 11/1993 | Kuroda et al. | |
| 5,282,797 A | 2/1994 | Chess | |
| 5,344,434 A | 9/1994 | Talmore | |
| 5,358,503 A | 10/1994 | Bertwell et al. | |
| 5,368,555 A | 11/1994 | Sussman et al. | |
| 5,401,270 A | 3/1995 | Muller et al. | |
| 5,405,368 A | 4/1995 | Eckhouse | |
| 5,441,495 A | 8/1995 | Liboff et al. | |
| 5,445,146 A | 8/1995 | Bellinger | |
| 5,445,608 A | 8/1995 | Chen et al. | |
| 5,447,528 A | 9/1995 | Gerardo | |
| 5,464,436 A | 11/1995 | Smith | |
| 5,474,528 A | 12/1995 | Meserol | |
| 5,501,655 A | 3/1996 | Roit et al. | |
| 5,503,637 A | 4/1996 | Kyricos et al. | |
| 5,511,563 A | 4/1996 | Diamond | |
| 5,540,737 A | 7/1996 | Fenn | |
| 5,562,719 A | 10/1996 | Lopez-Claros | |
| 5,571,152 A | 11/1996 | Chen et al. | |
| 5,580,550 A | 12/1996 | Gough et al. | |
| 5,580,555 A | 12/1996 | Schwartz | |
| 5,601,526 A | 2/1997 | Chapelon et al. | |
| 5,616,140 A * | 4/1997 | Prescott | 606/10 |
| 5,617,258 A | 4/1997 | Negus et al. | |
| 5,621,091 A | 4/1997 | Kunkel et al. | |
| 5,622,168 A | 4/1997 | Keusch et al. | |
| 5,627,870 A | 5/1997 | Kopecky | |
| 5,640,978 A | 6/1997 | Wong | |
| 5,643,334 A | 7/1997 | Eckhouse et al. | |
| 5,720,894 A | 2/1998 | Neev et al. | |
| 5,728,090 A | 3/1998 | Martin et al. | |
| 5,755,752 A | 5/1998 | Segal | |
| 5,762,867 A | 6/1998 | D'Silva | |
| 5,766,233 A | 6/1998 | Thiberg | |
| 5,769,878 A | 6/1998 | Kamei | |
| 5,800,479 A | 9/1998 | Thiberg | |
| 5,817,008 A | 10/1998 | Rafert et al. | |
| 5,830,208 A | 11/1998 | Muller | |
| 5,842,477 A | 12/1998 | Naughton et al. | |
| 5,843,073 A | 12/1998 | Sinofsky | |
| 5,849,585 A | 12/1998 | Mather et al. | |
| 5,871,521 A | 2/1999 | Kaneda et al. | |
| 5,879,376 A | 3/1999 | Miller | |
| 5,902,741 A | 5/1999 | Purchio et al. | |
| 5,928,207 A | 7/1999 | Pisano et al. | |
| 5,928,945 A | 7/1999 | Seliktar et al. | |
| 5,951,596 A | 9/1999 | Bellinger | |
| 5,954,762 A | 9/1999 | Di Mino et al. | |
| 5,958,761 A | 9/1999 | Yogev et al. | |
| 5,983,141 A | 11/1999 | Sluijter et al. | |
| 5,989,245 A | 11/1999 | Prescott | |
| 5,993,442 A | 11/1999 | Omori | |
| 6,013,096 A | 1/2000 | Tucek | |
| 6,015,404 A | 1/2000 | Altshuler et al. | |
| 6,027,495 A | 2/2000 | Miller | |
| 6,030,767 A | 2/2000 | Wagner et al. | |
| 6,033,431 A | 3/2000 | Segal | |
| 6,042,531 A | 3/2000 | Holcomb | |
| 6,045,575 A | 4/2000 | Rosen et al. | |
| 6,046,046 A | 4/2000 | Hassanein | |
| 6,059,820 A | 5/2000 | Baronov | |
| 6,060,306 A | 5/2000 | Flatt et al. | |
| 6,063,108 A | 5/2000 | Salansky et al. | |
| 6,074,411 A | 6/2000 | Lai et al. | |
| 6,084,242 A | 7/2000 | Brown et al. | |
| 6,100,290 A | 8/2000 | Levy et al. | |
| 6,107,325 A | 8/2000 | Chan et al. | |
| 6,107,608 A | 8/2000 | Hayes | |
| 6,112,110 A | 8/2000 | Wilk | |
| 6,117,128 A | 9/2000 | Gregory | |
| 6,129,748 A | 10/2000 | Kamei | |
| 6,143,878 A | 11/2000 | Koopman et al. | |
| 6,146,410 A | 11/2000 | Nagypal et al. | |
| 6,149,679 A | 11/2000 | Di Mino et al. | |
| 6,156,028 A | 12/2000 | Prescott | |
| 6,162,211 A | 12/2000 | Tankovich et al. | |
| 6,179,771 B1 | 1/2001 | Mueller | |
| 6,179,830 B1 | 1/2001 | Kokubu | |
| 6,187,210 B1 | 2/2001 | Lebouitz et al. | |
| 6,198,958 B1 | 3/2001 | Ives et al. | |
| 6,210,317 B1 | 4/2001 | Bonlie | |
| 6,210,425 B1 | 4/2001 | Chen | |
| 6,213,998 B1 | 4/2001 | Shen et al. | |
| 6,214,035 B1 | 4/2001 | Streeter | |
| 6,221,095 B1 | 4/2001 | Van Zuylen et al. | |
| 6,223,071 B1 | 4/2001 | Lundahl et al. | |
| 6,238,425 B1 | 5/2001 | Thiberg | |
| 6,264,649 B1 | 7/2001 | Whitcroft et al. | |
| 6,267,779 B1 | 7/2001 | Gerdes | |
| 6,267,780 B1 | 7/2001 | Streeter | |
| 6,273,884 B1 | 8/2001 | Altshuler et al. | |
| 6,273,885 B1 | 8/2001 | Koop et al. | |
| 6,273,905 B1 | 8/2001 | Streeter | |
| 6,277,974 B1 | 8/2001 | Lo et al. | |
| 6,290,713 B1 | 9/2001 | Russell | |
| 6,290,714 B1 | 9/2001 | Streeter | |
| 6,306,130 B1 | 10/2001 | Anderson et al. | |
| 6,312,451 B1 | 11/2001 | Streeter | |
| 6,344,050 B1 | 2/2002 | Chen | |
| 6,358,272 B1 | 3/2002 | Wilden | |
| 6,363,285 B1 | 3/2002 | Wey | |
| 6,364,907 B1 | 4/2002 | Obochi et al. | |
| 6,379,295 B1 | 4/2002 | Woo | |
| 6,379,376 B1 | 4/2002 | Lubart | |
| 6,391,023 B1 | 5/2002 | Weber et al. | |
| 6,395,016 B1 | 5/2002 | Oron et al. | |
| 6,397,107 B1 | 5/2002 | Lee et al. | |
| 6,402,678 B1 | 6/2002 | Fischell et al. | |
| 6,421,562 B1 | 7/2002 | Ross | |
| 6,432,101 B1 | 8/2002 | Weber et al. | |
| 6,436,094 B1 | 8/2002 | Reuter | |
| 6,440,121 B1 | 8/2002 | Weber et al. | |
| 6,443,974 B1 | 9/2002 | Oron et al. | |
| 6,443,977 B1 | 9/2002 | Jaillet | |
| 6,443,978 B1 | 9/2002 | Zharov | |
| 6,447,537 B1 | 9/2002 | Hartman | |
| 6,458,120 B1 | 10/2002 | Shen et al. | |
| 6,471,716 B1 | 10/2002 | Pecukonis | |
| 6,494,900 B1 | 12/2002 | Salansky et al. | |
| 6,508,813 B1 | 1/2003 | Altschuler et al. | |
| 6,511,475 B1 | 1/2003 | Altschuler et al. | |
| 6,514,220 B2 | 2/2003 | Melton, Jr. et al. | |
| 6,530,920 B1 | 3/2003 | Whitcroft et al. | |
| 6,537,301 B1 | 3/2003 | Kamei | |
| 6,537,302 B1 | 3/2003 | Thiberg | |
| 6,537,304 B1 | 3/2003 | Oron | |
| 6,542,524 B2 | 4/2003 | Miyake | |
| 6,551,308 B1 | 4/2003 | Muller et al. | |
| 6,554,853 B2 | 4/2003 | Chen | |
| 6,571,735 B1 | 6/2003 | Wilkinson | |
| 6,602,245 B1 | 8/2003 | Thiberg | |
| 6,602,274 B1 | 8/2003 | Chen | |
| 6,602,275 B1 | 8/2003 | Sullivan | |
| 6,632,219 B1 | 10/2003 | Baronov et al. | |
| 6,638,272 B2 | 10/2003 | Cho et al. | |
| 6,645,230 B2 | 11/2003 | Whitehurst | |
| 6,653,618 B2 | 11/2003 | Zenzie | |
| 6,663,659 B2 | 12/2003 | McDaniel | |
| 6,666,878 B2 | 12/2003 | Carlgren | |
| 6,679,877 B2 | 1/2004 | Ota et al. | |
| 6,685,702 B2 | 2/2004 | Quijano et al. | |
| 6,689,062 B1 | 2/2004 | Mesallum | |

| | | |
|---|---|---|
| 6,692,486 B2 | 2/2004 | Jaafar et al. |
| 6,692,517 B2 | 2/2004 | Cho et al. |
| 6,733,492 B2 | 5/2004 | Ota et al. |
| 6,743,222 B2 | 6/2004 | Durkin et al. |
| 6,746,473 B2 | 6/2004 | Shanks et al. |
| 6,770,069 B1 | 8/2004 | Hobart et al. |
| 6,817,997 B2 | 11/2004 | Furuno et al. |
| 6,832,111 B2 | 12/2004 | Tu et al. |
| 6,860,896 B2 | 3/2005 | Leber et al. |
| 6,866,678 B2 | 3/2005 | Shenderova et al. |
| 6,872,221 B2 | 3/2005 | Lytle |
| 6,878,144 B2 | 4/2005 | Altshuler et al. |
| 6,896,693 B2 | 5/2005 | Sullivan |
| 6,899,723 B2 | 5/2005 | Chen |
| 6,902,563 B2 | 6/2005 | Wilkens et al. |
| 6,918,922 B2 | 7/2005 | Oron |
| 6,921,413 B2 | 7/2005 | Mahadevan-Jansen et al. |
| 6,974,224 B2 | 12/2005 | Thomas-Benedict |
| 6,974,450 B2 | 12/2005 | Weber et al. |
| 6,974,451 B2 | 12/2005 | Altshuler et al. |
| 6,976,985 B2 | 12/2005 | Altshuler et al. |
| 7,037,326 B2 | 5/2006 | Lee |
| 7,041,094 B2 | 5/2006 | Connors et al. |
| 7,051,738 B2 | 5/2006 | Oron et al. |
| 7,054,676 B2 | 5/2006 | Hedlund et al. |
| 7,066,929 B1 | 6/2006 | Azar et al. |
| 7,070,611 B2 | 7/2006 | Biel |
| 7,077,840 B2 | 7/2006 | Altshuler et al. |
| 7,081,128 B2 | 7/2006 | Hart et al. |
| 7,083,610 B1 | 8/2006 | Murray et al. |
| 7,100,615 B1 | 9/2006 | Kert |
| 7,101,384 B2 | 9/2006 | Benedict |
| 7,118,563 B2 | 10/2006 | Weckwerth et al. |
| 7,150,710 B2 | 12/2006 | Haber et al. |
| 7,217,266 B2 | 5/2007 | Anderson et al. |
| 7,220,254 B2 | 5/2007 | Altshuler et al. |
| 7,282,060 B2 | 10/2007 | DeBenidictis et al. |
| 7,288,108 B2 | 10/2007 | DiMauro et al. |
| 7,303,578 B2 | 12/2007 | De Taboada et al. |
| 7,309,348 B2 | 12/2007 | Streeter et al. |
| 7,311,722 B2 | 12/2007 | Larsen |
| 7,311,723 B2 | 12/2007 | Seibel et al. |
| 7,316,922 B2 | 1/2008 | Streeter |
| 7,344,555 B2 | 3/2008 | Anders et al. |
| 7,351,252 B2 | 4/2008 | Altshuler et al. |
| 7,351,253 B2 | 4/2008 | DiMauro et al. |
| 7,389,776 B2 | 6/2008 | Maksimovich |
| 7,402,167 B2 | 7/2008 | Nemenov et al. |
| 7,412,141 B2 | 8/2008 | Gowda et al. |
| 7,463,916 B2 | 12/2008 | Kawasaki et al. |
| 7,534,255 B1 | 5/2009 | Streeter et al. |
| 7,559,945 B2 | 7/2009 | Breden et al. |
| 7,575,589 B2 | 8/2009 | De Taboada et al. |
| 7,695,469 B2 | 4/2010 | Boutoussov et al. |
| 7,695,504 B2 | 4/2010 | Anders et al. |
| 7,744,590 B2 | 6/2010 | Eells et al. |
| 7,848,035 B2 | 12/2010 | DeLapp et al. |
| 2001/0044623 A1 | 11/2001 | Chen |
| 2002/0029071 A1 | 3/2002 | Whitehurst |
| 2002/0068927 A1 | 6/2002 | Prescot |
| 2002/0087205 A1 | 7/2002 | Chen |
| 2002/0123781 A1 | 9/2002 | Shanks et al. |
| 2002/0156371 A1 | 10/2002 | Hedlund et al. |
| 2002/0161418 A1 | 10/2002 | Wilkens et al. |
| 2002/0188334 A1 | 12/2002 | Carlgren |
| 2002/0198575 A1 | 12/2002 | Sullivan |
| 2003/0004556 A1 | 1/2003 | McDaniel |
| 2003/0021124 A1 | 1/2003 | Elbrecht et al. |
| 2003/0023283 A1 | 1/2003 | McDaniel |
| 2003/0109906 A1 | 6/2003 | Streeter |
| 2003/0114872 A1 | 6/2003 | Mueller et al. |
| 2003/0125782 A1 | 7/2003 | Streeter |
| 2003/0125783 A1 | 7/2003 | Moran |
| 2003/0144712 A1 | 7/2003 | Streeter |
| 2003/0167080 A1 | 9/2003 | Hart et al. |
| 2003/0181962 A1 | 9/2003 | Streeter |
| 2003/0209906 A1 | 11/2003 | McCurdy et al. |
| 2003/0212442 A1 | 11/2003 | Streeter |
| 2003/0216797 A1 | 11/2003 | Oron |
| 2004/0010300 A1 | 1/2004 | Masotti et al. |
| 2004/0014199 A1 | 1/2004 | Streeter |
| 2004/0015214 A1 | 1/2004 | Simkin et al. |
| 2004/0030325 A1 | 2/2004 | Cahir et al. |
| 2004/0044384 A1 | 3/2004 | Leber et al. |
| 2004/0073278 A1 | 4/2004 | Pachys |
| 2004/0093042 A1 | 5/2004 | Altshuler et al. |
| 2004/0116909 A1 | 6/2004 | Neuberger et al. |
| 2004/0132002 A1 | 7/2004 | Streeter |
| 2004/0138727 A1 | 7/2004 | Taboada et al. |
| 2004/0153130 A1 | 8/2004 | Oron et al. |
| 2004/0153131 A1 | 8/2004 | Yorke |
| 2004/0158300 A1 | 8/2004 | Gardiner |
| 2004/0162596 A1 | 8/2004 | Altshuler et al. |
| 2004/0220513 A1 | 11/2004 | Streeter |
| 2004/0236226 A1 | 11/2004 | Maki et al. |
| 2004/0260367 A1 | 12/2004 | Taboada et al. |
| 2005/0005626 A1 | 1/2005 | McMahon |
| 2005/0009161 A1 | 1/2005 | Streeter |
| 2005/0024853 A1 | 2/2005 | Thomas-Benedict |
| 2005/0107851 A1 | 5/2005 | De Taboada et al. |
| 2005/0159793 A1 | 7/2005 | Streeter |
| 2005/0187595 A1 | 8/2005 | Streeter |
| 2005/0203595 A1 | 9/2005 | Oron |
| 2005/0216072 A1 | 9/2005 | Mahadevan-Jansen et al. |
| 2006/0155348 A1 | 7/2006 | deCharms |
| 2006/0167532 A1 | 7/2006 | Parker |
| 2006/0223155 A1 | 10/2006 | Streeter |
| 2006/0253177 A1 | 11/2006 | De Taboada et al. |
| 2007/0066996 A1 | 3/2007 | Katzman et al. |
| 2007/0114872 A1 | 5/2007 | Han |
| 2007/0129778 A1 | 6/2007 | Dougal |
| 2007/0162093 A1 | 7/2007 | Porter et al. |
| 2007/0179570 A1 | 8/2007 | De Taboada et al. |
| 2007/0260295 A1 | 11/2007 | Chen et al. |
| 2007/0288072 A1 | 12/2007 | Pascual-Leone et al. |
| 2008/0004565 A1 | 1/2008 | Streeter et al. |
| 2008/0033412 A1 | 2/2008 | Whelan et al. |
| 2008/0033513 A1 | 2/2008 | Man et al. |
| 2008/0051858 A1 | 2/2008 | Haber et al. |
| 2008/0070229 A1 | 3/2008 | Streeter |
| 2008/0077199 A1 | 3/2008 | Shefi et al. |
| 2008/0114419 A1 | 5/2008 | Crowley |
| 2008/0125836 A1 | 5/2008 | Streeter et al. |
| 2008/0140164 A1 | 6/2008 | Oberreiter et al. |
| 2008/0208297 A1 | 8/2008 | Gertner et al. |
| 2008/0221211 A1 | 9/2008 | Streeter |
| 2009/0054955 A1 | 2/2009 | Kopell et al. |
| 2009/0088680 A1 | 4/2009 | Aravanis et al. |
| 2009/0112280 A1 | 4/2009 | Wingeier et al. |
| 2009/0163982 A1 | 6/2009 | deCharms |
| 2009/0216301 A1 | 8/2009 | Streeter et al. |
| 2009/0222067 A1 | 9/2009 | Toselli et al. |
| 2009/0254068 A1 | 10/2009 | Karni et al. |
| 2009/0254154 A1 | 10/2009 | De Taboada et al. |
| 2009/0270776 A1 | 10/2009 | Chang |
| 2010/0010592 A1 | 1/2010 | De Taboada et al. |
| 2010/0010594 A1 | 1/2010 | De Taboada |
| 2010/0016841 A1 | 1/2010 | De Taboada |
| 2010/0067128 A1 | 3/2010 | Delapp |
| 2010/0094384 A1 | 4/2010 | De Taboada |
| 2010/0105977 A1 | 4/2010 | De Taboada et al. |
| 2010/0152820 A1 | 6/2010 | Anders et al. |
| 2010/0161017 A1 | 6/2010 | Choi et al. |
| 2010/0204762 A1 | 8/2010 | De Taboada et al. |
| 2010/0211136 A1 | 8/2010 | De Taboada et al. |
| 2011/0060266 A1 | 3/2011 | Streeter |
| 2011/0144723 A1 | 6/2011 | Streeter et al. |

FOREIGN PATENT DOCUMENTS

| | | |
|---|---|---|
| DE | 41 08 328 A1 | 9/1992 |
| DE | 42 13 053 A1 | 10/1993 |
| DE | 295 15 096 U1 | 1/1996 |
| EP | 0 130 950 | 4/1990 |
| EP | 0 763 371 A2 | 3/1997 |
| EP | 0 783 904 A2 | 7/1997 |
| EP | 0 827 716 | 3/1998 |
| EP | 1 074 275 | 2/2001 |
| EP | 1 226 787 A2 | 7/2002 |

| | | |
|---|---|---|
| EP | 2 082 696 | 7/2009 |
| JP | 04023634 | 2/1992 |
| WO | WO 92/03964 | 3/1992 |
| WO | WO 96/36397 | 11/1996 |
| WO | WO 96/36396 | 1/1997 |
| WO | WO 98/04321 | 2/1998 |
| WO | WO 98/22573 | 5/1998 |
| WO | WO 98/33556 | 8/1998 |
| WO | WO 99/42178 | 8/1999 |
| WO | WO 99/46005 | 9/1999 |
| WO | WO 99/62599 | 12/1999 |
| WO | WO 00/25684 | 5/2000 |
| WO | WO 00/35534 | 6/2000 |
| WO | WO 01/68172 | 9/2001 |
| WO | WO 02/37449 A1 | 5/2002 |
| WO | WO 02/055149 | 7/2002 |
| WO | WO 02/092509 | 11/2002 |
| WO | WO 02/098509 | 12/2002 |
| WO | WO 2005/025672 A1 | 3/2005 |
| WO | WO 2005/118067 A1 | 12/2005 |
| WO | WO 2006/024038 A2 | 3/2006 |
| WO | WO 2006/105254 | 10/2006 |
| WO | WO 2006/115761 | 11/2006 |
| WO | WO 2006/138659 | 12/2006 |
| WO | WO 2008/049905 | 5/2008 |
| WO | WO 2008/054812 | 5/2008 |
| WO | WO 2008/141296 | 11/2008 |
| WO | WO 2009/019710 | 2/2009 |
| WO | WO 2009/067323 A1 | 5/2009 |
| WO | WO 2010/009452 A1 | 1/2010 |
| WO | WO 2010/031777 | 3/2010 |

OTHER PUBLICATIONS

U.S. Appl. No. 10/723,171, filed Nov. 26, 2003, Streeter.

Agov, B. S., et al., "On the mechanism of therapeutic action of helium-neon laser in ischemic heart disease", *Klin Med* (Mosc), pp. 102-105, 1985 (Abstract only).

Arvidsson, Andreas, et al., "Neuronal replacement from endogenous precursors in the adult rat brain after stroke", *Nature Medicine*, vol. 8, No. 9, Sep. 2002, pp. 963-970.

Asahi, Minoru, et al., Expression of Interleukin B Converting Enzyme Gene Family and bc1-2 Gene Cerebral Family in the Rat Brain Following Permanent Occlusion of the Middle Cerebral Artery, *Journal of Blood Flow & Metabolism*, vol. 17, No. 1, Jan. 1997.

Assia, E. et al., "Temporal Parameters of Low Energy Laser Irradiation for Optimal Delay of Post-Traumatic Degeneration of Rat Optic Nerve", Brain Research, vol. 476, 1989, pp. 205-212.

Basford, Jeffrey R., M.D., Ph.D., "Lasers in Orthopedic Surgery—Laser Therapy: Scientific Basis and Clinical Role", May 1993, vol. 16, No. 5, pp. 541-547.

Belkin, M. et al., "A Critical Review of Low Energy Laser Bioeffects", Lasers and Light in Ophthalmology, vol. 2, No. 1, pp. 63-71, 1988.

Bevilacqua et al.; "In Vivo Local Determiniation of Tissue Optical Properties: Applications to the Human Brain"; *Applied Optics*; vol. 28, No. 22; Aug. 1, 1999; pp. 4939-4950.

Bibikova, A. et al., "Enhancement of Muscle Regeneration in the Toad (*Bufo viridis*) Gastrocnemius Muscle by Low-Energy Laser Irradiation", The Anatomical Reocrd, vol. 235, 1993, pp. 374-380.

Bibikova, A. et al., "Enhancement of Angiogenesis in Regenerating Gastroenemius Muscle of the Toad (*Bufo viridis*) by Low-Energy Laser Irradiation", Anatomy and Embryology (1994), vol. 190, pp. 597-602. Aug.

Brazzle, John, et al., Active Microneedles with Integrated Functionality, *Technical Digest of the 2000 Solid-State Sensor and Actuator Workshop*, Department Of Bioengineering, University of Utah, Salt Lake City, Utah 84112 (five pages) (2000).

Brill, G.E., et al., Modifying influence of low level laser irradiation on the relationships in endothelial cell—blood platelet system, *10th Congress of the European Society for Photobiology*, Vienna, Austria (one page). Jun. 8, 2004.

Byrnes, K.R., et al., Light Therapy Promotes Axonal Regeneration After Acute Spinal Cord Injury in Adult Rats, Program No. 275.2, *Society for Neuroscience*, 2003, Abstract.

Chance et al.: "Comparison of Time-Resolved and -Unresolved Measurements of Deoxyhemoglobin in Brain"; *Proc. Natl Acad. Sc.i USA*; vol. 85; ul. 1988; pp. 4971-4975.

Cohen, Michael A., Method of Forming Microneedles and other Micron-Scale Transdermal Probes, Office of Technology Licensing, University of California, Berkeley, Abstract (two pages) Dec. 5, 2003.

Conlan, M.J. et al., Biostimulation of Wound Healing by Low-Energy Laser Irradiation:, Journal of Clin. Periodontology, vol. 23, 1996, pp. 492-496.

Dirnagl, Ulrich, et al., Pathobiology of ischaemic stroke: an integrated view, *TINS*, vol. 22, No. 9, 1999, pp. 391-397.

Dobson, J., et al., Theory and Applications of a Magnetic Force Bioreactor, *European Cells and Materials*, vol. 4, Suppl. 2, 2002 (pp. 42-44).

Eells, J.T., et al., Therapeutic photobiomodulation for methanol-induced retinal toxicity, *Proceedings National Academy of Science* (*PNAS*), vol. 100, No. 6, Mar. 18, 2003, pp. 3439-3444.

Elimadi, Aziz, et al., Trimetazidine Counteracts the Hepatic Injury Associated with Ischemia-Reperfusion by Michondrial Function, *Journal of Phamacology and Experimental Therapeutics*, vol. 286, No. 1, 1998, pp. 23-28.

Firbank et al.; "A Theoretical Study of the Signal Contributions of Regions of the Adult Head to Near-Infrared Spectroscopy Studies of Visual Evoked Responses"; *Neuroimage*; No. 8; 1998; pp. 69-78.

Fisher, M., "Characterizing the Target of Acute Stroke Therapy", Stroke, 1997, vol. 28, pp. 866-872.

Gage, Fred H., Brain, Repair Yourself, *Scientific American*, Sep. 2003, pp. 47-53.

Gasparyan, Levon V., Biochemical and Biophysical Effects of Low Level Laser Irradiation, *MAL 2000*, Helsinki, Finland (three pages), Sep. 28-30, 2000.

Gasparyan, Levon V., et al., Low Level Laser Therapy of Male Genital Tract Chronic Inflammations, *WALT 2-nd Congress* (Kansas City, USA), 1998 (two pages).

Gasparyan, Levon V., et al., The influence of LED irradiation at different wavelengths on functional activity of blood platelets, *10th Congress of the European Society of Photobiology*, Vienna, Austria, 2003 (one page). September.

Gasparyan, Levon V., et al., The influence of LED irradiation at different wavelengths with antioxidants on functional activity of blood platelets, Laser, Florence, 2003 (one page).

Gasparyan, Levon V., Experience of Russian (former USSR) Scientists in LLLT and UV Blood Irradiation, *MAL 2000*, Helsinki, Finland (four pages), Sep. 28-30, 2000.

Gasparyan, Levon V., Investigation of Sensations, Associated with Laser Blood Irradiation, *WALT 2-nd Congress* (Kansas City, USA), 1998 (two pages).

Gasparyan, Levon V., Millimeter Wave Therapy, *MAL 2000*, Helsinki, Finland (three pages). Sep. 28-30, 2000.

Gordon, G. A., "The Use of low power lasers in sports medicine", *Clinical Sports Medicine 2*, 53-61 (1990). September.

Gross, Garrett J., et al., Mechanisms of Postischemic Contractile Dysfunction, Myocardial Protection From Surgical Ischemic-Reperfusion Injury, *An International Symposium*, Asheville, North Carolina, Sep. 21-24, 1997, pp. 1898-1904. (aka Hammon).

Iadecola, Costantino, et al., Inhibition of inducible nitric oxide synthase ameliorates ischemic damage, *Am. J. Physiol.*, vol. 268, 1995, pp. R286-R292.

Karu, T.I., Low power laser therapy, in *Biomedical Photonics Handbook*, Ch. 48, Editor-in-Chief Tuan Vo-Dinh, Boca Raton, CRC Press, 2003. September.

Karu, Tiina, Mechanisms of interaction of monochromatic visible light with cells, *Proc. SPIE*, vol. 2630, pp. 2-9, 1996. September.

Karu, Tiina, Mechanisms of Low-Power Laser Light Action on Cellular Level, Effects of Low-Power Light on Biological Systems V, *Proceedings of SPIE*, Jul. 7, 2000, vol. 4159 pp. 1-17.

Karu, Tiina, Photobiological Fundamentals of Low Power Laser Therapy, *IEEE Journal of Quantum Electronics*, vol. QE-23, No. 10, Oct. 1987, pp. 1703-1717.

Karu, et al., Biostimulation of HeLa Cells by Low-Intensity Visible Light. II. Stimulation of DNA and RNA Synthesis in a Wide Spectral Range. Il Nuovo Cimento. (1984) p. 309-318. October.

Laser Exchange: Delivering the medicine of the future, 42 pages, Oct. 13, 2004.

Leung, Mason C.P., et al., Treatment of Experimentally Induced Transient Cerebral Ischemia with Low Energy Laser Inhibits Nitric Oxide Synthase Activity and Up-Regulates the Expression of Transforming Growth Factor-Beta 1, *Laser in Surgery and Medicine*, 31:283-288 (2002).

Lychagov, Vladislav V., et al. Experimental study of NIRtransmittance of the human skull, *Proc. of SPIE*, vol. 6085, 2006 (five pages).

Mester, E., et al., Effect of Laser Rays on Wound Healing, *The American Journal of Surgery*, vol. 122, Oct. 1971, pp. 532-535.

Mochizuki-Oda, Noriko, et al., Effects of near-infra-red laser irradiation on adenosine triphosphate and adenosine diphosphate contents of rat brain tissue, *Neuroscience Letters 323*, May 3, 2002, pp. 207-210.

Nishioka, Norman S., et al., Reflection and Transmission of Laser Light From the Esophagus: The Influence of Incident Angle, *Gastroenterology*, vol. 94, 1988, pp. 1180-1185. November.

Nissan, M. et al., "HeNe Laser Irradiation Delivered Transcutaneously: Its Effect on the Sciatic Nerve of Rats", Lasers in Surgery and Medicine, vol. 6, pp. 435-438, Nov. 1986.

Olesin, Al, et al., Laser irradiation of venous blood for production of reperfusion syndrome in myocardial infarction, *Patologisheskaia fiziologiia*, Sep-Dec. 1992 (5-6) p20-3, ISSN 0031-2991 Journal Code: 0376421, English abstract of Russian article) November.

Oron, Uri, et al., Attenuation of Infarct Size in Rats and Dogs after Myocardial Infarction by Low-Energy Laser Irradiation, *Lasers in Surgery and Medicine*, vol. 28, 2001, pp. 204-211.

Oron, Uri, et al., Low-Energy Laser Irradiation Reduces Formation of Scar Tissue After Myocardial Infarction in Rats and Dogs, *Circulation*, vol. 103, Jan. 16, 2001, pp. 296-301.

Park, James L., Ph.D., et al., Mechanisms of Myocardial Reperfusion Injury, The Annals of Thoracic Surgery, *Official Journal of Thoracic Surgeons and the Southern Thoracic Surgical Association*, vol. 68, No. 5, Nov. 1999, pp. 1905-1912.

International Search Report for PCT/CA99/00156, dated Jun. 11, 1999.

International Search Report and Written Opinion for PCT/US2007/002219, dated Jul. 5, 2007.

International Preliminary Report on Patentability for PCT/US2007/002219, dated May 2, 1998.

International Search Report and Written Opinion for PCT/US2007/002474, dated Sep. 27, 2007.

International Preliminary Report on Patentability for PCT/US2007/002474, dated Apr. 16, 2008.

International Search Report for PCT/US02/36808, dated Apr. 2, 2003.

International Search Report for PCT/US03/00747, dated May 14, 2003.

International Preliminary Report on Patentability for PCT/US04/029724, dated Mar. 23, 2006.

International Preliminary Report on Patentability for PCT/US2005/004873, dated Sep. 14, 2006.

International Search Report and Written Opinion for PCT/US2005/004873, dated Sep. 5, 2005.

Physical Therapy, The Efficacy of Laser Therapy for Musculoskeletal and Skin Disorders: A Criteria-Based Metanalysis of Randomized Clinical Trials, vol. 72, No. 7, Jul. 1992, pp. 483/12-491/21.

Pogue et al.: "Comparison of Image Geometries for Diffuse Optical Tomography of Tissue"; *Optics Express*; vol. 4, No. 8; Apr. 12, 1999; pp. 270-286.

Semenza, Gregg L., et al., Regulation of Mammalian O2 Homeostatis by Hypoxia-Inducible Factor 1, *Ann. Rev. Cell Dev. Biol.*, vol. 15, 1999, pp. 551-578.

Smith, Kendric C., "The Photobiological Basis of Low Level Laser Radiation Therapy", *Photobiological Basis of LLLT*, pp. 1-7, 1991.

Stys, Peter K., Anoxis and Ischemic Injury of Myelinated Axons in CNS White Matter: From Mechanistic Concepts to Therapeutics, *J. Cereb. Blood Flow Metab.*, vol. 18, No. 1, Jan. 1998, 42 pages (037C1 lists pp. 2-25).

Thor: Is LLT Different from Ultrasound?, 2 pages, Oct. 13, 2004.

Thor, Specification, 30mW Red Laser probe, web page (1 page), Oct. 6, 1999.

Thor Laser, 100mW, Thor, Illt, LLLT, Low Level Laser Therapy, low level laser therapy, Lazer, Thorl., Oct. 6, 1999, p. 1.

Thor, Specification, 200mW/810nm Laser probe, Oct. 6, 2009.

Thor, Specification, 200mW/650nm Laser probe, Oct. 6, 1999.

Thor, Specification, 500mW/810nm Laser probe, page (1 page), Oct. 6, 1999.

Thor Laser, Specifications, Thor: Specifications, Thor, lllt, LLLT, Low Level Laser Therapy, low level laser therapy, Oct. 6, 1999, pp. 1-2.

Thor: Product List, Thor, lllt, LLLT, Low Level Laser Therapy, Laz., Oct. 6, 1999, pp. 1-4.

Toon, John, Taking the "Ouch" Out of Needles: Arrays of Micron-Scale "Microneedles" Offer New Technique for Drug Delivery, *Georgia Tech Research News*, Jun. 22, 1998 (three pages).

Toricelli, P., et al., Laser Biostimulation of cartilage: in vitro evaluation, *Biomed. Pharmacother.*, 2001, vol. 55, pp. 117-120. Oct.

Tuchin, Valery, Tissue Optics: Light Scattering Methods and Instruments for Medical Diagnosis, SPIE Press, Tutorial Texts in *Optical Engineering*, vol. TT38, 2000, pp. 3-11, 2000.

Tunér, Jan, et al., Low Level Laser Therapy, Clinical Practice and Scientific Background, Prima Books in Sweden AB, 1999, pp. 1-9, 45-58, 62-114, 113-116, 118, 132-134, 134-135, 149-151, 151-156, 185, 334-364. Oct.

Van Breugel, Hans H.F.I., et al., Power Density and Exposure Time of He-Ne Laser Irradiation are More Important than Total Energy Dose in Photo-Biomoducation of Human Fibroblasts InVitro, *Lasers in Surgery and Medicine* (1992), Wiley-Liss, Inc., pp. 528-537.

Van Breugel, H.H.F.I., Bar, P.R., "He-Ne Laser Irradiation Affects Profileration of Cultered Rat Schwann Cells in Dose-dependent Manner," 1993, Journal of Neurocytology, 22, 185-190.

Weiss, N. et al., "Enhancement of Muscle Regeneration in the Rat Gastrocnemius Muscle by Low Energy Laser Irradiation", Anat. Embroyl. (1992), vol. 186, pp. 497-503. January.

Wong-Riley, Margaret T.T., et al., Light-emitting diode treatment reverse the effect of TTX on cytochrome oxidase in neurons, *NeuroReport*, vol. 12, No. 14, Oct. 8, 2001, pp. 3033-3037.

Yaakobi, Tali, et al., Long-term effect of low energy laser irradiation on infarction and reperfusion injury in the rat heart, *J. Appl. Physiol.*, vol. 90, 2001, pp. 2411-2419. January.

EPO Extended Search Report re EP Application No. 09170679.6, dated Jan. 4, 2010. in 6 pages.

"Is Laser Therapy Overtaking Ultrasound?" http://www.laser.uk.com/laser, Therapy vs. ultrasound.html, dated Feb. 20, 1999.

"Laser Exposure Limits & Hazard Calculations," Excerpts from OSHA Technical Manual, Chapter 6: Laser Hazards, date unknown.

Accelrys, "Optical Absorption Spectra of Melanins—a Comparison of Theoretical and Experimental Results," Chemicals Case Study, Accelyrys, Oct. 5, 2005, http://accelrys.com/references/case-studies/archive/studies/melanins_partll.pdf.

Adamic, Metka et al., "Vascular lasers and IPLS: Guidelines for care from the European Society for Laser Dermatology (ESLD)," Journal of Cosmetic and Laser Therapy, 2007; 9: 113-124.

Albertini, R. et al., "COX-2 mRNA expression decreases in the subplantar muscle of rat paw subjected to carrageenan-induced inflammation after low level laser therapy," Inflammation Research, 56 (2008) pp. 228-229.

Albrecht-Buehler, Guenter. "Reversible, excitation light-induced enhancement of fluorescence of live mammalian mitochondria," The FASEB Journal, vol. 14, Oct. 2000, pp. 1864-1866.

Alerstam, Erik et al., "Parallel computing with graphics processing units for high-speed Monte Carlo simulation of photon migration," Journal of Biomedic Optics, vol. 13(6), Nov./Dec. 2008.

Amat, Albert et al., "Modification of the intrinsic fluorescence and the biochemical behavior of ATP after irradiation with visible and near-infrared laser light," Journal of Photochemistry and Photobiology B: Biology 81 (2005) 26-32.

Anders et al., Low power laser irradiation alters the rate of regeneration of the rat facial nerve, Laser Surg. Med., 13:72-82 (1993).

Anders, Juanita J., "The Potential of Light Therapy for Central Nervous System Injury and Disease," Photomedicine and Laser Surgery, vol. 27, No. 3 (2009) pp. 379-380.

Anonymous, "Engineer, heal thyself," News Brief, Optoelectronics Report 3, www.optoelectronics-world.com, Nov. 1, 1999.

Ataullakhanov et al. "What Determines the Intracellular ATP Concentration," Bioscience Reports, vol. 22, No. 5 and 6, Oct. and Dec. 2002.

Avni, Dorit et al., "Protection of Skeletal Muscles from Ischemic Injury: Low-Level Laser Therapy Increases Antioxidant Activity", Photomedicine and Laser Surgery vol. 23, No. 3, 2005, p. 273-277.

Barnett, Alex H. et al., "Robust inference of baseline optical properties of the human head with three-dimensional segmentation from magnetic resonance imaging," Applied Optics, vol. 42, No. 16, Jun. 1, 2004, pp. 3095-3108.

Bashkatov, A.N. et al., "Estimate of the melanin content in human hairs by the inverse Monte-Carlo method using a system for digital image analysis," Quantum Electronics 36(12) 1111-1118 (2006).

Baxter, Richard, "Laser Safety Training Manual," University of Chicago Chemistry Department, date unknown.

Beauvoit, B. et al. "Contribution of the Mitochondrial Compartment to the Optical Properties of the Rat Liver: A Theoretical and Practical Approach," Biophysical Journal, vol. 67, Dec. 1994, pp. 2501-2510.

Ben-Shachar, Dorit et al., "Neuroanatomical Pattern of Mitochondrial Complex I Pathology Varies between Schizophrenia, Bipolar Disorder and Major Depression," PLoS One, Nov. 2008, vol. 3, Issue 11.

Bisland, Stuart K. et al., "To begin at the beginning: The science of bio-stimulation in cells and tissues," Proc. of SPIE, vol. 6140, 2006.

Boelens, R. et al., "EPR Studies of the Photodissociation Reactions of Cytochrome c Oxidase-Nitric Oxide Complexes," Biochimica et Biophysica Acta, 679 (1982) pp. 84-94.

Boelens, Rolf et al., "An EPR Study of the Photodissociation Reactions of Oxidised Cytochrome c Oxidase-Ntiric Oxide Complexes," Biochimica et Biophysica Acta, 924 (1983) pp. 176-183.

Bonnet, Sébastien et al., "A Mitochondria-K+ Channel Axis Is Suppressed in Cancer and Its Normalization Promotes Apoptosis and Inhibits Cancer Growth," Cancer Cell 11, 37-51, Jan. 2007.

Borutaite, Vilmante et al., "Reversal of nitric oxide-, peroxynitrite- and S-nitrosothiol-induced inhibition of mitochondrial repiration or complex I activity by light and thiols," Biochimica et Biophysica Acta, 1459, (2000) pp. 405-412.

Brain Injury Source, vol. 3, Issue 4 (1999).

Brennan, Angela M. et al., "NADPH oxidase is the primary source of superoxide induced by NMDA receptor activation," Nature Neuroscience, vol. 12, No, 7, Jul. 2009, pp. 857-864.

Brown, G.C., "Mechanisms of inflammatory neurodegeneration: iNOS and NADPH oxidase," Biochemical Society Transactions (2007) vol. 35, part 5, pp. 1119-1121.

Bruch, Reinhard. "Low Level Laser Therapy (LLLT)," Nevada Health Forum, Dec. 4, 2003.

Buckman, Jennifer F. et al., "Spontaneous Changes in Mitochondrial Membrane Potential in Cultured Neurons," The Journal of Neuroscience, Jul. 15, 2001, 21(14): 5054-5065.

Bullock, M. Ross et al., "Outcome measures for clinical trials in neurotrauma," Neurosurg. Focus 13 (1): Jul. 2002, pp. 1-11.

Calabrese, Vittorio et al., "Nitric oxide in the central nervous system: neuroprotection versus neurotoxicity," Nature Reviews: Neuroscience, vol. 8, Oct. 2007, pp. 766-775.

Carroll, James D., "A 3D dose model for low level laser/led therapy biostimulation and bioinhibition," Proc. of SPIE, vol. 6846, 2008.

Carroll, James S et al., "Red Blood Cell Stimulation of Platelet Nitric Oxide Production Indicated by Quantitative Monitoring of the Communication between Cells in the Bloodstream," Analytical Chemistry, vol. 79, No. 14, pp. 5133-5138, Jul. 15, 2007.

Castello, Pablo et al., "Oxygen-regulated isoforms of cytochrome c oxidase have differential effects on its nitric oxide production and on hypoxic signaling," PNAS Early Edition, www.pnas.org/cgi/doi/10.1073/pnas.0709461105, 2008.

Catanzaro et al. "Managing Tissue Heating in Laser Therapy to Enable Double-Blind Clinical Study," Proc. SPIE, vol. -6140, 614000 (2006).

Celsi, Fulvio et al., "Mitochondria, calcium and cell death: A deadly triad in neurodegeneration," Biochim. Biophys. Acta., May 2009; 1787(5): 335-344.

Chan, C. Savio et al., "Rejuvenation protects neurons in mouse models of Parkinson's disease," Nature, vol. 447, Jun. 28, 2007.

Chen, Aaron Chih-Hao et al., "Low Level Laser Therapy activates NF-kB via Generation of Reactive Oxygen Species in Mouse Embryonic Fibroblasts," Proc. of SPIE, vol. 7165, 2009.

Chen, James et al., "New Technology for Deep Light Distribution in Tissue for Phototherapy," The Cancer Journal, vol. 8, No. 2, Mar./Apr. 2002, pp. 154-163.

Chiros Equipment Supplies, "Erchonia The healing light," http://www.chiros.com/au.erchonia.php, Accessed Feb. 7, 2002.

Chow, Roberta T. et al., "830nm laser irradiation induces varicosity formation, reduces mitochondrial membrane potential and blocks fast axonal flow in small and medium diameter rat dorsal root ganglion neurons: implications for the analgesic effect of 830nm laser," Journal of the Peripheral Nervous System, 12:28-39 (2007).

Custo, Anna et al., "Comparison of Diffusion and Transport in human head," date unknown.

Custo, Anna et al., "Effective scattering coefficient of the cerebral spinal fluid in adult head models for diffuse optical imaging," Applied Optics, vol. 45, No. 19, Jul. 1, 2006, pp. 4747-4756.

Dawson, Elizabeth et al., "Adverse Events Associated With Nonablative Cutaneous Laser, Radiofrequency, and Light-Based Devices," Seminars in Cutaneous Medicine and Surgery, 2007, pp. 15-21.

de Groot, A.C. et al., "Bijwerkingen van Lasertherapie," Nederlands Tijdschrift voor Dermatologie & Venereologie, vol. 16, Sep. 2006 (In Dutch).

Delori, François et al., "Maximum permissible exposures for ocular safety (ANSI 2000), with emphasis on ophthalmic devices," J. Opt. Soc. Am. A., vol. 24, No. 5, May 2007, pp. 1250-1265.

Demaurex, Nicolas et al., "Reactive oxygen species are NOXious for neurons," Nature Neuroscience, vol. 12, No. 7, Jul. 2009, pp. 819-820.

Desmet, et al.: "Clinical and Experimental Applications of NIR-LED Photobiomodulation"—Photomedicine and Laser Surgery—2006;24(2): 121-128.

Dhar, Shilpa S. et al., "Chromosome Conformation Capture of all 13 Genomic Loci in the Transcriptional Regulation of the Multi-subunit Bigenomic Cytochrome C Oxidase in Neurons," The Journal of Biological Chemistry. 2009.

Fisher, M., "Characterizing the Target of Acute Stroke Therapy", Stroke, 1997, vol. 28, pp. 866-872.

Franceschini, Maria Angela et al., "Near-Infrared Absorption and Scattering Spectra of Tissues in Vivo," date unknown.

Frigo, Lucio et al., "The effect of low-level laser irradiation (Ga-Al-AsP—660nm) on in vitro and in vivo melanoma," http://www.biomedcentral.com/1471-2407/9/404, Nov. 20, 2009.

Galuzzi, Lorenzo et al., "Targeting post-mitochondrial effectors of apoptosis for neuroprotection," Biochim. Biophys. Acta (2008), doi:10.1016/lbbabio.2008.09.006.

Gao, Zuejuan et al., "Molecular mechanisms of cell proliferation induced by low power laser irradiation," Journal of Biomedical Science, 16:4, 2009.

Gasparyan, Levon et al., "Activation of Angiogenesis Under Influence of Red Low Level Laser Radiation," Laser Florence, 2004, pp. 1-8.

Giuliani, Alessandro et al., "Low infra red laser light irradiation on cultured neural cells: effects on mitochondria and cell viability after oxidative stress," BMC Complementary and Alternative Medicine 2009, 9:8.

Go-Jo, Inc., (2002). "Watch for 'Subtle Energies' Featuring 'Dr. Larry Lytle," Flyer, South Dakota.

Goldstein, Larry B. et al., "Patient Safety in Trials of Therapy for Acute Ischemic Stroke," The Journal of the American Medical Association, vol. 287, No. 8, Feb. 27, 2002.

Gourley, Paul L. et al., "Optical Phenotyping of Human Mitochondria in a Biocavity Laser," IEEE Journal of Selected Topics in Quantum Electronics, vol. 11, No. 4, Jul./Aug. 2005.

Haitsma, Iain K. et al., "Monitoring cerebral oxygenation in traumatic brain injury," Progress in Brain Research, vol. 161, Chapter 14, pp. 207-216, 2007.

Hamblin et al. "Mechanisms of Low Level Light Therapy," Proc. of SPIE, vol. 6140 614001-1 (2006).

Hancock, Celeste M. et al., "Modulation of Pain in Osteoarthritis: The Role of Nitric Oxide," Clin. J. Pain, vol. 24, No. 4, May 2008, pp. 353-365.

Harris, David M et al., "Laser Biostimulation: Review and Hypothesis," Laser Topics, 1988, pp. 9-14.

Häusser, Michael et al., "Controlling neural circuits with light," Nature: News & Views, vol. 446, Apr. 5, 2007, pp. 617-619.

Hawkins, Denise et al., "How Long After Laser Irradiation Should Cellular Responses be Measured to Determine the Laser Effects?" Journal of Laser Applications, vol. 19, No. 2, May 2007, pp. 74-83.

Hawkins-Evans, Denise et al., "Effect of Wavelength and Fluence on Morphology, Cellular and Genetic Integrity of Diabetic Wounded Human Skin Fibroblasts," Proc. of SPIE vol. 6140, p. 614006-1 to 614006-13.

Hawkins-Evans, Denise et al., "Efficacy of a single high does versus multiple low doses of LLLT on wonded skin fibroblasts," Proc. of SPIE vol. 6632, p. 66321U-1 to 66321U-12.

Hilf, Russell, "Mitochondria are targets of photodynamic therapy," J. Bioenerg. Biomembr. (2007) 39:85-89.

Hollenbeck, Peter J., "The Pattern and Mechanism of Mitochondrial Transport in Axons," Frontiers in Bioscience 1, Jul. 1, 1996.

Hori, Yasuaki et al., "Automatic characterization and segmentation of human skin using three-dimensional optical coherence tomography," Optics Express, vol. 14, No. 5, 6 Mar. 2006, pp. 1862-1877.

Hu, Wan-Ping et al., "Helium-Neon Laser Irradiation Stimulates Cell Proliferation through Photostimulatory Effects in Mitochondria," Journal of Investigative Dermatology (2007), vol. 127, pp. 2048-2057.

Hüttemann, Maik et al., "Regulation of oxidative phosphorylation, the mitochondrial membrane potential, and their role in human disease," J. Bioenerg. Biomembr (2008) 40:445-456, pp. 445-456.

Ilev, i., et al., "Smart optical fiber probes for precise tissue treatment," Proc. SPIE, 4616:220-228 (2002).

Ilic, S., et al.: "Effects of Power Densities, Continuous and Pulse Frequencies, and Number of Sessions of Low-Level Laser Therapy on Intact Rat Brain" Photomedicine and Laser Surgery—2006; 24(4): 458-466.

INVOS® Cerebral Oximeters, Mallinckrodt (2000).

Ionto Comed® Product Brochure, date unknown, (In Greek).

Jacques, Steven L. "Skin Optics," Oregon Medical Laser Center News, Jan. 1998, http://omlc.ogi/edu/news/jan98/skinoptics.html.

Jacques, Steven L. et al., "Tutorial on diffuse light transport," Journal of Biomedical Optics, 13(4), 041302 (Jul./Aug. 2008).

Jekabsone, Aiste et al., "Nitric oxide from neuronal nitric oxide synthase sensitises neurons to hypoxia-induced death via competitive inhibition of cytochrome oxidase," Journal of Neurochemistry, 2007.

Jou, Shaw-Hwa et al., "Mitochondrial Dysfunction and Psychiatric Disorders," Chang Gung Med. J., vol. 32, No. 4, Jul.-Aug. 2009, pp. 370-379.

Kahn, Fred et al. "Low Intensity Laser Therapy: The clinical approach," Proc. of SPIE, vol. 6140, 2008.

Kaplan, Michael, "The Theralaser," date unknown.

Karrer et al., Long Pulsed Dye Laser for Photodynamic Therapy: Investigations in Vitro and in Vitro; Lasers in surg & Med.: vol. 25; pp. 51-59 (1999).

Karu et al. "Cell Attachment to Extracellular Matrices is Modulated by Pulsed Radiation at 820 nm and Chemicals that Modify the Activity of Enzymes in the Plasma Membrane," Lasers in Surgery and Medicine, 29: 274-281 (2001).

Karu, T.I., "Cellular mechanisms of low-power laser therapy," Proc. of SPIE, vol. 5149, 2003, pp. 60-66.

Karu, Tiina I, "Mitochondrial Signaling in Mammalian Cells Activated by Red and Near-IR Radiation," Photochemistry and Photobiology, 2008, 84: 1091-1099.

Karu, Tiina I. et al., "A Novel Mitochondrial Signaling Pathway Activated by Visible-to-near Infrared Radiation," Photochemistry and Photobiology, 2004, 80: 366-372.

Karu, Tiina I. et al., "Cellular Effects of Low Power Laser Therapy Can be Mediated by Nitric Oxide," Lasers in Surgery and Medicine, 36:307-314 (2005).

Karu, Tiina I. et al., "Changes in absorbance of monolayer of living cells induced by laser irradiation at 633, 670, and 820 nm," Proc. of SPIE, vol. 4431, 2002, pp. 306-312.

Karu, Tiina I. et al., "Irradiation with a diode at 820 nm induces changes in circular dichroism spectra (250-780 nm) of living cells," Proc. of SPIE, vol. 4433, 2001, pp. 97-102.

Karu, Tiina, "Primary and secondary mechanisms of action of visible to near-IR radiation on cells," Journal of Photochemistry and Photobiology, 49 (1999) pp. 1-17.

Karu, Tiina, "Primary mechanisms of action of low-intensity laser light on cells," SPIE, vol. 3829, 1999, pp. 42-53.

Karu, Tiina. "Can a mechanism based on changes in redox properties of cytochrome c oxidase be crucial in explaining of low-power laser effects?" SPIE, vol. 3732, 1999. pp. 202-213.

Khodjakov, Alexey et al., "Laser micro-irradiation of mitochondria: is there an amplified mitochondrial death signal in neural cells?" Mitochondrion 3 (2004) pp. 217-227.

Kiguchi, Masashi et al., "Comparison of light intensity on the brain surface due to laser exposure during optical topography and solar irradiation," Journal of Biomedical Optics 12(6), Nov./Dec. 2007.

Kim, Kyunghan et al., "Ultrafast Laser Radiation and Conduction Heat Transfer in Biological Tissues," Proceedings of IMECE2005, 2005 ASME International Mechanical Engineering Congress and Exposition, Nov. 5-11, 2005.

Kofke, W. Andrew et al., "Near Infrared Laser Therapy," University of Pennsylvania, 2009.

Lam, T.S., et al.: "Laser stimulation of collagen synthesis in human skin fibroblast cultures," Lasers Life Sci, 1:61-77 (1986).

Lampl, Yair, "Laser treatment for stroke," Expert Rev. Neurotherapeutics 7(8), 2007.

Lane, Nick "Power Games" Nature/vol. 443/26 Oct. 2006, Nature Publishing Group, pp. 901-903.

Lapchak, Paul A. "Transcranial Near-Infrared Laser Therapy Improves Behavior and Differentially Regulates the Expression of Rapid Response Elements (Genes) in Rabbits Following Embolic Strokes," Stroke 2009; 40; e214; Abstracts From the 2009 International Stroke Conference.

Lapchak, Paul A. et al., "Advances in ischemic stroke treatment: neuroprotective and combination therapies," Expert Opin. Emerging Drugs, Mar. 2007, vol. 12, No. 1, pp. 97-112.

Lapchak, Paul A. et al., "Safety Profile of Transcranial Near-Infrared Laser Therapy Administered in Combination with Thrombolytic Therapy to Embolized Rabbits," Stroke, Nov. 2008.

Lasermedics, Inc., "The Effects of the Microlight 830 on Repetitive Stress Injuries," Aug. 4, 1993.

Li, Ming-jun, "Managing nonlinearity in optical fiber for high-power lasers," The International Society for Optical Engineering, SPIE Newsroom, 2006.

Liang, et al.,: "Photobimodulation Partially Rescues Visual Cortical Neurons from Cyanide-Induced Apoptosis"—Neuroscience 2006;139: 639-649.

Liesz, Arthur et al., "Regulatory T cells are key cerebroprotective immunomodulators in acute experimental stroke," Nature Medicine, Jan. 25, 2009.

Lievens, P.O, "The Effect of I.R. Laser Irradiation on the Vasomotricity of the Lymphatic System," Lasers in Medical Science, vol. 5:189, 1991.

Lisman et al. "Two Light-Induced Processes in the Photoreceptor Cells of Limulus Ventral Eyes," The Journal of General Physiology, vol. 58, pp. 544-561, 1971.

Liu, Timon Cheng-Yi et al., "Cellular rehabilitation of photobiomodulation," Proc. of SPIE, vol. 6534, 2007.

Lohr, Nicole L. et al., "Enhancement of nitric oxide release from nitrosyl hemoglobin and nitrosyl myoglobin by red/near infrared radiation: Potential role in cardioprotection," Journal of Molecular and Cellular Cardiology 47 (2009) 256-263.

Lopes-Martins, Rodrigo Alvaro Brendão et al, "Steroids block the anti-inflammatory effects of low level laser therapy," Proc. of SPIE, vol. 6140, 2006.

Low-Level Laser Therapy: Compu-Lase, Spectra-Medics Pty Ltd—Low-Level Laser Therapy Specialists, http://www.spectra-medics.com/compulase.html, 1998.

Lubart, Rachel et al., "Broadband Visible Light Induced NO Formation," 2009, http://proceedings.aip.org/proceedings/cper.jsp.

Lubart, Rachel et al., "Low-Energy Laser Irradiation Promotes Cellular Redox Activity," Photomedicine and Laser Surgery, vol. 23, No. 1, 2005, pp. 3-9.

Luo, Gang-Yue et al, "Membranotropic photobiomodulation on red blood cell deformability," Proc. of SPIE, vol. 6534, 2007.

Lychagov, V. V., et al.: "Experimental study of cadavers head transmittance", Saratov Fall Meeting 2004: Optical Technologies in Biophysics and Medicine VI, Proc. of SPIE vol. 5771, pp. 328-331.

Macklis, Jeffrey D., "Transplanted Neocrotical Neurons Migrate Selectively into Regions of Neuronal Degeneration Produced by Chromophore-targeted Laser Photolysis," The Journal of Neuroscience, Sep. 1993, 13(9); 3848-3863.

Maegawa, Yasuyo et al., "Effects of Near-Infrared Low-Level Laser Irradiation on Microcirculation," Lasers in Surgery and Medicine, 27:427-437 (2000).

Marshall, Laura S., "Hope after failure in clinical trials," BusinessScan, BioPhotonics, Apr. 2009.

Martin, Joan B., "Light Activated Tissue Regeneration and Therapy," Notes, Aug. 2004.

Mason, Maria G. et al., "Nitric oxide inhibition of respiration involves both competitive (heme) and noncompetitive (copper) binding to cytochrome c oxidase," PNAS, vol. 103, pp. 708-713, Jan. 9, 2006.

Matas et al. "Eliminating the Issue of Skin Color in Assessment of the Blanch Response," Advances in Skin & Wound Care, vol. 14 (4, Part 1 of 2), pp. 180-188, Jul./Aug. 2001.

McClelland, Robyn L. et al., "Neurologic Correlates of Infarction-Like Lesion Location on Magnetic Resonance Imaging in the Cardiovascular Health Study," Journal of Stroke and Cerebrovascular Disease, vol. 9, No. 5, Sep.-Oct. 2000; pp. 218-228.

McKinlay, A.F. et al., "Biological Bases of Maximum Permissible Exposure Levels of Laser Standards," J. Soc. Radiol. Prol. 4 (1), 1984.

Meguro, Toshinari et al., "Caspase Inhibitors Attenuate Oxyhemoglobin-Induced Apoptosis in Endothelial Cells," Stroke, 2001; 32; 561-566.

Mester, Endre et al., "The Biomedical Effects of Laser Application," Lasers in Surgery and Medicine, 5:31-39 (1985).

Mirsky, N. et al., "Promotion of Angiogenesis by Low Energy Laser Irradiation," Antioxidants & Redox Signaling, vol. 4, No. 5, 2002, pp. 785-791.

Mochizuki-Oda, Noriko et al., "Effects of Near-Infrared Laser on Neural Cell Activity," American Institute of Physics, 2004, pp. 192-195.

Mohanty, Samarendra Kumar et al., "Generation of ROS in cells on exposure to CW and pulsed near-infrared laser tweezers," Photochemical & Photobiological Sciences, 2006, pp. 134-139.

Molinaro, M., "Light/Tissue Interaction IST 8A," Lecture #5, Jan. 23, 2006.

Moncada, Salvador et al., "Nitric oxide, cell bioenergetics and neurodegeneration," Journal of Neurochemistry, 2006, 97, pp. 1676-1689.

Moriyama, Yumi et al., "In Vivo Study of the Inflammatory Modulating Effects of Low-level Laser Therapy on iNOS Expression Using Bioluminescence Imaging," Photochemistry and Photobiology, 2005, 81: 1351-1355.

Moser, Christopher C. et al., "Darwin at the molecular scale: selection and variance in electron tunneling proteins including cytochrome c oxidase," Philosophical Transactions of the Royal Society B, 2006, 361: 1295-1305.

Mthunzi, Patience et al., "Influence of Beam Shape on in-vitro Cellular Transformations in Human Skin Fibroblasts," Proc. of SPIE, vol. 5876, 2005.

Mudra, R. et al., "Analysis of near-infrared spectroscopy and indocyanine green dye dilution with Monte Carlo simulation of light propagation in the adult brain," Journal of Biomedical Optics, 11(4), Jul./Aug. 2006.

Myers, D.R. et al., "Proposed Reference Spectral Irradiance Standards to Improve Concentrating Photovoltaic System Design and Performance Evaluation," National Renewable Energy Laboratory, May 2002.

Naviaux, Robert K., "Mitochondria-Light Interactions—Mechanisms of Cell Sparing and Regeneration," The Mitochondrial and Metabolic Disease Center, 2007.

Ng, Kwan-Hoong, "Non-Ionizing Radiations—Sources, Biological Effects, Emissions and Exposures," Proceedings of the International Conference on Non-Ionizing Radiation at UNITEN, Electromagnetic Fields and Our Health, Oct. 20-22, 2003.

Nilsson, Thomas, "Photoinduced electron transfer from tris(2,2'-bipyridyl)ruthenium to cytochrome c oxidase," Proc. Natl. Acad. Sci. USA 89 (1992) pp. 6497-6501.

Okada, Eiji et al, "Near-infrared light propagation in an adult head model. II. Effect of superficial tissue thickness on the sensitivity of the near-infrared spectroscopy signal," Applied Optics, Jun. 1, 2003, vol. 42, No. 16, pp. 2915-2922.

Oron, Uri et al.: Low-Level Laser Therapy Applied Transcranially to Rats After Induction of Stroke Significantly Reduces Long-Term Neurological Deficits, Stroke, 2006; 37:2620-2624.

Osipov, A.N. et al., "Biological Activity of Hemoprotein Nitrosyl Complexes," Biochemistry, 2007, vol. 72, No. 13, pp. 1491-1504.

Palacios-Callender, Miriam et al., "Cytochrome c-oxidase regulates endogenous nitric oxide availability in respiring cells: A possible explanation for hypoxic vasodilation," PNAS, Nov. 20, 2007, vol. 104, No. 47, pp. 18508-18513.

Parathath, Susana R. et al., "Nitric Oxide Synthase Isoforms Undertake Unique Roles During Excitotoxicity," Stroke 2007; 38; 1938-1945.

Passarella, S., et al.: "Increase in the ADP/ATP Exchange in Rat Liver Mitochondria Irradiated in Vitro by Helium-Neon Laser", Biochemical and BioPhysical Research Communications, vol. 156, No. 2, Oct. 31, 1988, pp. 978-986.

Peterson, Jill et al., "Material Properties of the Human Cranial Vault and Zygoma," The Anatomical Record Part A, 274A:785-797 (2003).

Pislea, Mihaela et al., "Low Level Long Wavelength Laser Irradiation Effects on Cells Cycle Progression and Apoptosis of Energy Restricted Jurkat T-Cells," Romanian J. Biophys., vol. 19, No. 1, pp. 1-18, 2009.

Pogue, BW et al., "Transient absorption changes in vivo during photodynamic therapy with pulsed-laser light," British Journal of Cancer (1999) 80(3/4), pp. 344-351.

Popp, Fritz-Albert, "On the Coherence of Ultraweak Photon Emission from Living Tissues," Disequilibrium and Self-Organisation, pp. 207-230, 1986.

Respond 2400 Laser Therapy System, http://www.nmia.com/~pegasus/las2400.html, Accessed Nov. 3, 1998.

Respond Systems, Inc., "Understanding Low Level Laser Therapy," 1991.

Reznikov, L.L. et al., "The Biomechanism of Low-Energy Laser Irradiation is Similar to General Adaptive Reaction," Proc. SPIE, vol. 2086, 380 (1994).

Rochkind, S. et al., "New trend in neuroscience: Low-power laser effect on peripheral and central nervous system (basic science, preclinical and clinical studies)," Neurological Research, vol. 14, Mar. 1992, pp. 2-11.

Rose, Andreas et al., "Mode Field Pertubations and Numerical Aperture Broadening Due to Angular Misalignment in Multimode Fiber Coupling," Proc. of SPIE, vol. 7173, 2009.

Schaffer, Chris B. et al., "Two-Photon Imaging of Cortical Surface Microvessels Reveals a Robust Redistribution in Blood Flow after Vascular Occlusion," PLOS Biology, Feb. 2006, vol. 4, Issue 2, pp. 0258-0270.

Scheele, Jürgen S. et al., "Kinetics of NO Ligation with Nitric-oxide Synthase by Flash Photolysis and Stopped-flow Spectrophotometry," The Journal of Biological Chemistry, vol. 274, No. 19, May 1999, pp. 13105-13110.

Seremet, Teofila et al., "Photobiomodulation of Quercetin Antiproliferative Effects Seen in Human Acute Leukemia Jurkat Cells," Romanian J. Biophys., vol. 17, No. 1, pp. 33-43, 2007.

Sharpe, Martyn A., "Interaction of Peroxynitrite with Mitochondrial Cytochrome Oxidase," The Journal of Biological Chemistry, vol. 273, No. 47, Nov. 20, 1998, pp. 30961-30972.

Shichita, Takashi et al., "Pivotal role of cerebral interleukin-17-producing γδT cells in the delayed phase of ischemic brain injury," Nature Medicine, vol. 15, No. 8, Aug. 2009, pp. 946-951.

Shimada, Sachihiro et al., "Intracellular disruption of mitochondria in a living HeLa cell with 76-MHz femtosecond laser oscillator," Optics Express, vol. 13, No. 24, Nov. 28, 2005, pp. 9869-9880.

Shiva, Struti, "Shining a light on tissue NO stores: Near infrared release of NO from nitrite and nitrosylated hemes," Journal of Molecular and Cellular Cardiology, 46, 2009, pp. 1-3.

Sieron, A. et al., "Our Own Experience in Clinical Use of Low Power Laser Therapy," Przegl Lek, 1995; 52(1):13-5.

Sim-Med Ltd, Laser Therapy Manufacturers, www.therapylaser.com, date unknown.

Siposan, Dan G. et al., "Effect of Low-Level Laser Radiation on Some Rheological Factors in Human Blood: An in Vitro Study," Journal of Clinical Laser Medicine & Surgery, vol. 18, No. 4, 2000, pp. 185-195.

Smith, Rich, "Seeing the Light: How light therapy is surprising skeptics and gaining converts," Physical Therapy Products, Apr./May 2004.

Snyder, S.K., et al., "Quantitation of calcitonin gene-related peptide mRNA and neuronal cell death in facial motor nuclei following axotomy and 633 nm low power laser treatment," Surg. Med., 31:216-222 (2002).

Soane, Lucian et al., "Mechanisms of Impaired Mitochondrial Energy Metabolism in Acute and Chronic Neurodegenerative Disorders," J. Neurosci. Res., 2007, Nov. 15; 85(15): 3407-3415.

Sofiano Bros Ltd., Medical Laser, date unknown.

Sommer, A, et al., "Biostimulatory Windows in Low-Intensity Laser Activation: Lasers, Scanners, and NASA's Light-Emitting Diode Array System," Journal of Clinical Laser Medicine & Surgery, vol. 19, No. 1, 2001, pp. 29-33.

Stoll, Christian et al., "Quantum Dots on Gold: Electrodes for Photoswitchable Cytochrome c Electrochemistry," Small Journal, 2006, vol. 2, No. 6, pp. 741-743.

Stopp, Sebastian et al., "A new concept for navigated laser surgery," Laser Med. Sci. (2008) 23:261-266.

Sukstanskii, A.L. et al., "An analytical model of temperature regulation in human head," Journal of Thermal Biology, 29 (2004), pp. 583-587.

Super Lizer™, Spot Type Polarized Light Therapy Equipment Model HA-550, Tokyo Iken Co., Ltd. (date unknown).

Szundi, Istvan et al., "Flash-Photolysis of Fully Reduced and Mixed-Valence CO-Bound Rhodobacter sphaeroides Cytochrome c Oxidase: Heme Spectral Shifts," Biochemistry, 2007, 46, 12567-12578.

Tafur, Joseph et al., "Low-Intensity Light Therapy: Exploring the Role of Redox Mechanisms," Photomedicine and Laser Surgery, vol. 26, No. 4, 2008.

Tajima, H. et al., "A light-emitting diode fabricated from horse-heart cytochrome c," Solid State Communications, 126 (2003) 579-581.

The Laser Exchange, "LEDS," http://laser.uk.com/tech/index.html, Accessed Jan. 24, 2000 (p. 1 missing).

Theralase Inc., "Low Level Light Therapy (LLLT)," 1999.

Theralase Inc., "Therapeutic Lasers," date unknown.

Theralase Inc., "Therapeutic Medical Laser Summary," date unknown.

Therapeutic Laser Corporation, "Healing Light Healing the World," website unknown, Accessed Jul. 1, 1999.

Thor Models LX, DDII & DD, Accessed Jul. 1, 1999.

Thor: Product List, Thor, lllt, LLLT, Low Level Laser Therapy Equipment (LLLT), Laser Drive Untes, http://www.thorlaser.com/prodlist/index.html webpage (4 pages).

Toricelli, P., et al., Laser Biostimulation of cartilage: in vitro evaluation, Biomed. Pharmacother., Oct. 2001, vol. 55, pp. 117-120.

Trimmer, Patricia A. et al., "Reduced axonal transport in Parkinson's disease cybrid neurites is restored by light therapy," Molecular Neurodegeneration 2009, 4:26.

Troy, Tamara L. et al., "Optical Properties of Human Skin in the NIR Wavelength Range of 1000-2200nm," Instrumental Metrics, Inc., date unknown.

Tuchin, V., Optical Properties of Tissues With Strong (Multiple) Scattering, Tissue Optics, Light Scattering Methods and Instruments for Medical Diagnosis, SPIE Press, Bellingham, WA 2000 (2000), pp. 3-11.

Tunér, Jan et al., "It's All in the Parameters: A Critical Analysis of Some Well-Known Negative Studies on Low-Level Laser Therapy," Journal of Clinical Laser Medicine & Surgery, vol. 16, No. 5, 1998, pp. 245-248.

Tunér, Jan, et al., Low Level Laser Therapy, Clinical Practice and Scientific Background, Prima Books in Sweden AB, Oct. 1999, pp. 1-9, 45-58, 62-114, 113-116, 118, 132-134, 134-135, 149-151, 151-156, 185, 334-364.

Vakoc, Benjamin J. et al., "Real-time microscopic visualization of tissue response to laser thermal therapy," Journal of Biomedical Optics, Mar./Apr. 2007, vol. 12(2).

Verkruysse, Wim et al., "Infrared Measurement of Human Skin Temperature to Predict the Individual Maximum Safe Radiant Exposure (IMSRE)," Lasers in Surgery and Medicine, 39:757-766, 2007.

Villringer, Arno et al., "Non-invasive optical spectroscopy and imaging of human brain function," TINS vol. 20, No. 10, 1997.

Vladimirov, Yu. A. et al., "Molecular and Cellular Mechanisms Triggered by Low-level Laser Irradiation," Biophysics, vol. 49, No. 2, 2004, pp. 325-336.

Vladimirov, Yu. A. et al., "Photobiological Principles of Therapeutic Applications of Laser Radiation," Biochemistry (Moscow), vol. 69, No. 1, 2004, pp. 81-90.

Waynant, R., et al., "Review of Laser Therapy: Current Status and Consensus for Research Needed for Further Progress," NAALT Conference 2003.

Wells, Jonathan et al., "Biophysical Mechanisms of Transient Optical Stimulation of Peripheral Nerve," Biophysical Journal, vol. 93, Oct. 2007, pp. 2567-2580.

Wong-Riley, et al.: "Photobiomodulation Directly Benefits Primary Neurons Functionally Inactivated by Toxins", The Journal of Biological Chemistry—2005;280(6): 4761-4771.

Yang, Fu-Shou, "Medical Applications of Low Power Lasers in China," Laser Systems for Photobiology and Photomedicine, 1991, pp. 115-127.

Yaroslaysky, A. N. et al., "Optical properties of selected native and coagulated human brain tissues in vitro in the visible and near infrared spectral range," Physics in Medicine and Biology, 47 (2002), pp. 2059-2073.

Yi, Muqing et al., "Control of mitochondrial motility and distribution by the calcium: a homeostatic circuit," The Journal of Cell Biology, vol. 167, Nov. 22, 2004, pp. 661-672.

Young, A.E.R. et al., "Behaviour of near-infrared light in the adult human head: implications for clinical near-infrared spectroscopy," British Journal of Anaesthesia, 84 (1): 38-42 (2000).

Yujung, Kang et al., "Development of the fully automated program system; Can calculate transporting light intensity to the specific position in the brain tissue," http://pbil.kaist.ac.kr/lectures/bis500/report/proposal/team3_proposal_final.doc, accessed Apr. 30, 2007.

Zeischegg, Peter M., "Low Level Laser Therapy (LLLT)," http://www.drz.org/laser.htm, Accessed Oct. 1, 1999.

Zenzie et al. "Evaluation of Cooling Methods for Laser Dermatology," Lasers in Surgery and Medicine, 26:130-144 (2000).

Zhang, Rong et al., "Near infrared light protects cardiomyocytes from hypoxia and reoxygenation injury by a nitric oxide dependent mechanism," Journal of Molecular and Cellular Cardiology, 46 (2009) pp. 4-14.

\* cited by examiner

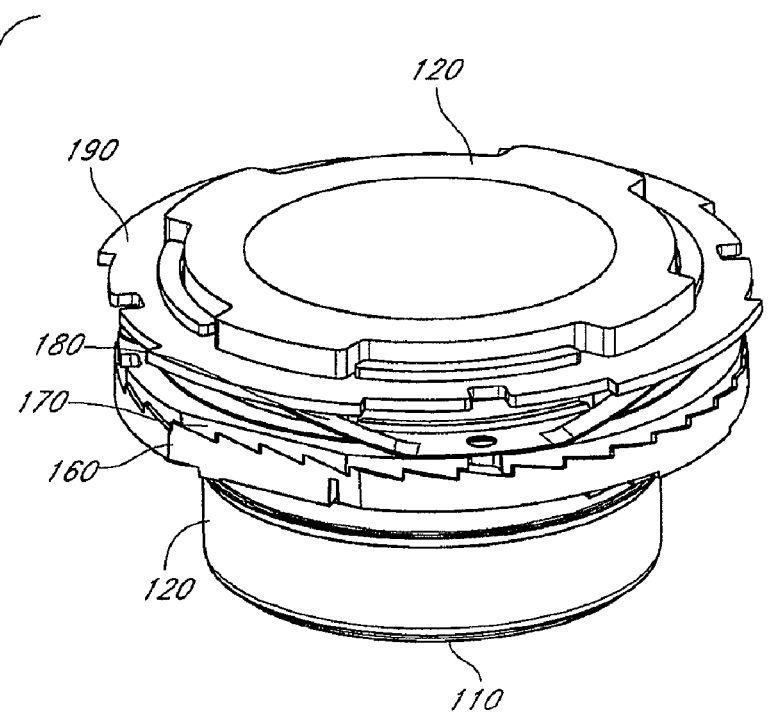
FIG. 14B
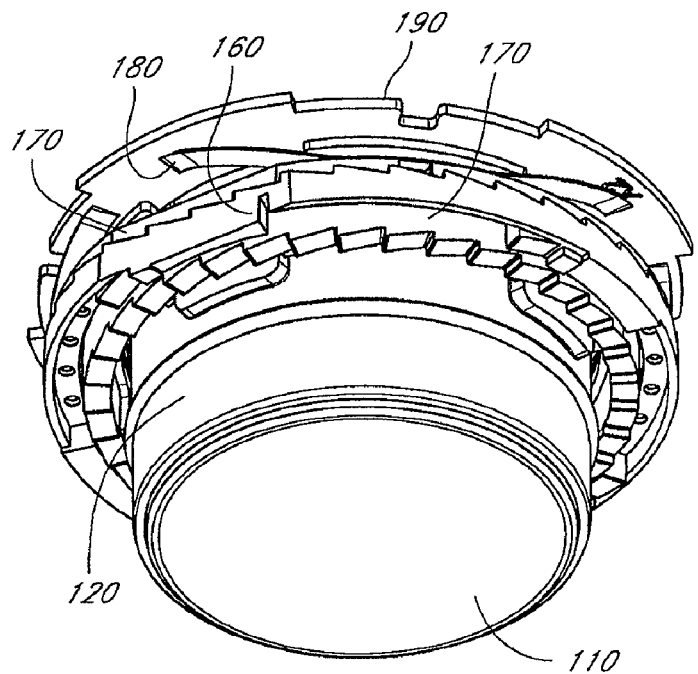

SINGLE USE LENS ASSEMBLY

RELATED APPLICATIONS

This application is a continuation of U.S. patent application Ser. No. 12/233,498, filed Sep. 18, 2008, and incorporated in its entirety by reference herein.

BACKGROUND OF THE INVENTION

1. Field of the Invention

This application relates generally to devices and methods used to irradiate portions of a patient's body with electromagnetic radiation.

2. Description of the Related Art

For treatment of various conditions or maladies (e.g., ischemic stroke), laser light is applied to a selected portion of the human body (e.g., the scalp) by pressing an optical assembly against the body and irradiating the body with laser light from a light delivery apparatus. To avoid unduly heating the irradiated tissue, the irradiated portion of the body can be cooled during irradiation by a portion of the optical assembly in contact with the body. The possibility of cross-contamination between subsequently-treated patients can be a concern in such instances.

SUMMARY

In certain embodiments, an optical assembly is releasably mountable to a light delivery apparatus comprising at least one heat dissipating surface. The optical assembly comprises an output optical element comprising a thermally conductive and optically transmissive material. The optical assembly further comprises a thermal conduit in thermal communication with the output optical element and comprising at least one surface configured to be in thermal communication with the at least one heat dissipating surface. The optical assembly further comprises a coupling portion configured to be placed in at least two states comprising a first state and a second state. In the first state, the coupling portion is attached to the light delivery apparatus such that the at least one surface of the thermal conduit is in thermal communication with the at least one heat dissipating surface of the light delivery apparatus. In the second state, the coupling portion is detached from the light delivery apparatus after having been attached to the light delivery apparatus in the first state and in which the coupling portion is configured to prevent re-attachment of the coupling portion to the light delivery apparatus.

In certain embodiments, an optical element is releasably mountable to a mounting portion of a light delivery apparatus. The optical element comprises a coupling portion adapted to be coupled to the mounting portion of the light delivery apparatus. The coupling portion is configured to be placed in at least two states comprising, a first state and a second state. In the first state, the coupling portion is attached to the light delivery apparatus. In the second state, the coupling portion is detached from the light delivery apparatus after having been attached to the light delivery apparatus in the first state and in which the coupling portion is configured to prevent re-attachment of the coupling portion to the light delivery apparatus.

In certain embodiments, a light delivery apparatus comprises a mounting portion and an optical element releasably mountable to the mounting portion. The optical element is adapted to be in at least two states comprising a first state and a second state. In the first state, the optical element is attached to the mounting portion. In the second state, the optical element is detached from the mounting portion after having been attached to the mounting portion in the first state and the optical element is configured to prevent re-attachment of the optical element to the mounting portion.

In certain embodiments, an optical assembly is releasably mountable to a light delivery apparatus comprising at least one heat dissipating surface. The optical assembly comprises an optical element comprising a thermally conductive and optically transmissive material. The optical assembly further comprises a thermal conduit in thermal communication with the output optical element and comprising at least one surface configured to be in thermal communication with the at least one heat dissipating surface. The optical assembly further comprises a coupling portion configured to releasably mount to the light delivery apparatus such that the at least one surface of the thermal conduit is in thermal communication with the at least one heat dissipating surface by rotating relative to and engaging a corresponding portion of the optical assembly without the at least one surface of the thermal conduit rotating relative to the at least one heat dissipating surface.

In certain embodiments, a light delivery apparatus has at least one heat dissipating surface. The light delivery apparatus comprises a mounting portion and an optical assembly. The optical assembly comprises an optical element comprising a thermally conductive and optically transmissive material. The optical assembly further comprises a thermal conduit in thermal communication with the optical element and comprising at least one surface configured to be in thermal communication with the at least one heat dissipating surface. The optical assembly further comprises a coupling portion configured to releasably mount to the mounting portion such that the at least one surface of the thermal conduit is in thermal communication with the at least one heat dissipating surface by rotating relative to and engaging a corresponding portion of the light delivery apparatus without the at least one surface of the thermal conduit rotating relative to the at least one heat dissipating surface.

In certain embodiments, a method releasably mounts an optical assembly to a light delivery apparatus comprising at least one heat dissipating surface. The method comprises providing an optical assembly adapted to be in at least two states comprising a first state and a second state. In the first state, the optical assembly is attached to the light delivery apparatus. In the second state, the optical assembly is detached from the light delivery apparatus after having been attached to the light delivery apparatus in the first state and the optical assembly is configured to prevent re-attachment of the optical assembly to the light delivery apparatus. The method further comprises attaching the optical assembly to the light delivery apparatus. The method further comprises detaching the optical assembly from the light delivery apparatus.

BRIEF DESCRIPTION OF THE DRAWINGS

FIG. 14B schematically illustrates two perspective views of the example optical assembly of FIG. 14A with the first element totally removed.

DETAILED DESCRIPTION

To reduce the probability of cross-contamination, the optical assembly of certain embodiments described herein is advantageously releasably mounted to the light delivery apparatus, thereby allowing the optical assembly to be (i) sterilized or otherwise cleaned separate from the light delivery apparatus, or (ii) disposed of after a single use. The optical assembly can be configured to be attached or affixed to the light delivery apparatus, and after the patient's body has been irradiated, the optical assembly can be detached or removed from the light delivery apparatus. In certain "single-use" embodiments, after being removed, the optical assembly of certain embodiments is configured to not be re-attachable to the light delivery apparatus.

Figure 1:
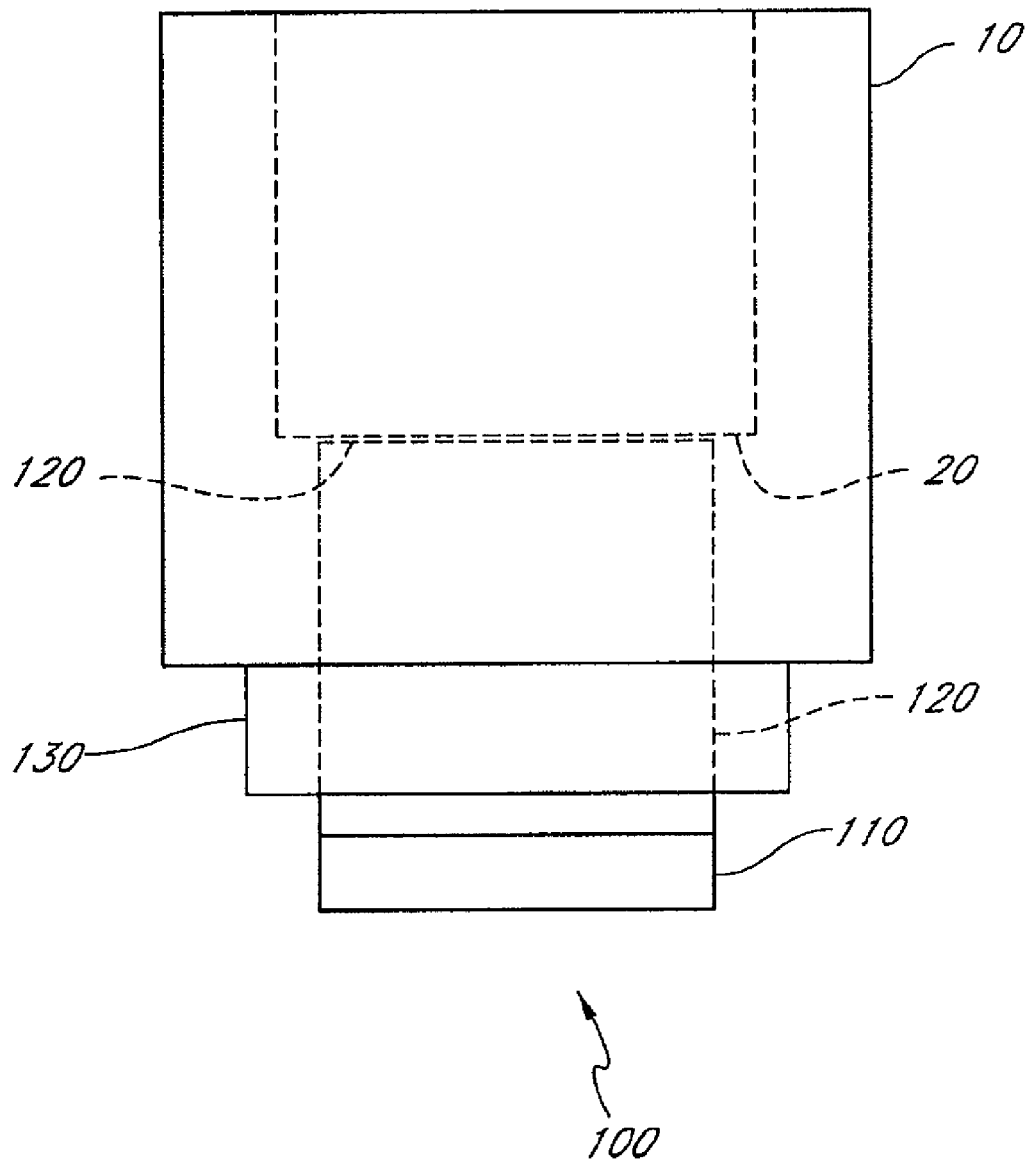
FIG. 1 schematically illustrates an optical assembly in accordance with certain embodiments described herein.

FIG. 1 schematically illustrates an optical assembly 100 in accordance with certain embodiments described herein. The optical assembly 100 is releasably mountable to a light delivery apparatus 10 comprising at least one heat dissipating surface 20. The optical assembly 100 comprises an output optical element 110 comprising a thermally conductive and optically transmissive material. The optical assembly 100 further comprises a thermal conduit 120 in thermal communication with the output optical element 110 and comprising at least one surface 122 configured to be in thermal communication with the at least one heat dissipating surface 20. The optical assembly 100 further comprises a coupling portion 130 configured to be placed in at least two states. In a first state of the at least two states, the coupling portion 130 is attached to the light delivery apparatus 10 such that the at least one surface 122 of the thermal conduit 120 is in thermal communication with the at least one heat dissipating surface 20 of the light delivery apparatus 10. In a second state of the at least two states, the coupling portion 130 is detached from the light delivery apparatus 10 after having been attached to the light delivery apparatus 10 in the first state and in which the coupling portion 130 is configured to prevent re-attachment of the coupling portion 130 to the light delivery apparatus 10.

In certain embodiments, the light delivery apparatus 10 is configured to deliver light to a portion of a patient's body. For example, in certain embodiments, the light delivery apparatus 10 is configured for treatment of a patient's brain by irradiating a portion of the patient's scalp with a predetermined wavelength and power density of laser light (e.g., as described in U.S. Pat. No. 7,303,578, which is incorporated in its entirety by reference herein).

Figure 2:
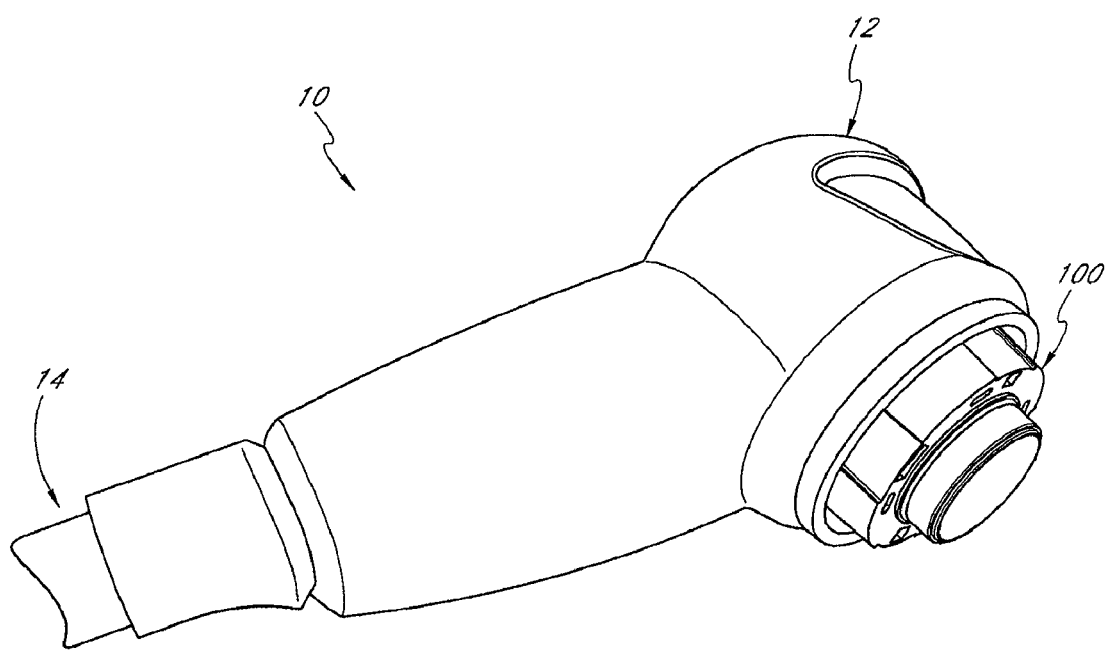
FIG. 2 schematically illustrates a light delivery apparatus compatible with certain embodiments described herein.

In certain embodiments, as schematically illustrated by FIG. 2, the light delivery apparatus 10 comprises a housing 12 which is optically coupled to a light source (e.g., a laser) via an optical conduit 14. In certain embodiments, the housing 12 is sized to be hand-held during operation.

The at least one heat dissipating surface 20 of the light delivery apparatus 10 in certain embodiments comprises a thermally conductive material (e.g., copper, aluminum, or other metal) which is in thermal communication with a cooling system (not shown). The cooling system in accordance with certain embodiments described herein utilizes one or more cooling mechanisms, including, but not limited to, a reservoir containing a cooling material (e.g., a cryogen), a conduit through which a cooling liquid (e.g., water) flows, a thermoelectric device, and a refrigerator. During operation of the light delivery apparatus 10, the at least one heat dissipating surface 20 is cooled such that thermal energy from the optical assembly 100 is dissipated away from the at least one heat dissipating surface 20.

In certain embodiments, the output optical element 110 comprises a material which is substantially thermally conductive and which is substantially optically transmissive to light emitted by the light delivery apparatus 10 (e.g., light in the wavelength range of 600 nanometers to 2000 nanometers, light in an infrared wavelength range). Example materials for the output optical element 110 include but are not limited to, sapphire, diamond, and calcium fluoride. In certain embodiments, the output optical element 110 comprises a lens having at least one curved surface (e.g., convex or concave) through which the light from the light delivery apparatus 10 is transmitted. In certain other embodiments, the output optical element 110 comprises a window having two substantially planar surfaces. In certain embodiments, the output optical element 110 comprises a diffuser which diffuses the light transmitted through the output optical element 110.

In certain embodiments, the thermal conduit 120 comprises a thermally conductive material (e.g., copper, aluminum, or other metal). In certain such embodiments, the at least one surface 122 of the thermal conduit 120 comprises the thermally conductive material. For example, in certain embodiments, the thermal conduit 120 comprises at least one of aluminum, nickel, and zinc. In certain embodiments in which the thermal conduit 120 comprises aluminum, the at least one surface 122 is anodized, while in certain other embodiments, the thermal conduit 120 comprises a nickel plating. In certain embodiments, the thermal conduit 120 is constructed of a single unitary piece, while in certain other embodiments, the thermal conduit 120 comprises a plurality of portions which are coupled or affixed together. In certain embodiments, the thermal conduit 120 is bonded to the output optical element 110 (e.g., by a thermally conductive material, by press fitting, by swaging, by metal injection, or by a collet spring). The thermal conduit 120 of certain embodiments is in thermal communication with the output optical element 110 and has sufficient thermal conductivity such that the output optical element 110 is cooled by the at least one heat dissipating surface 20 of the light delivery apparatus 10 when the optical assembly 100 is mounted to the light delivery apparatus 10.

Figure 3:
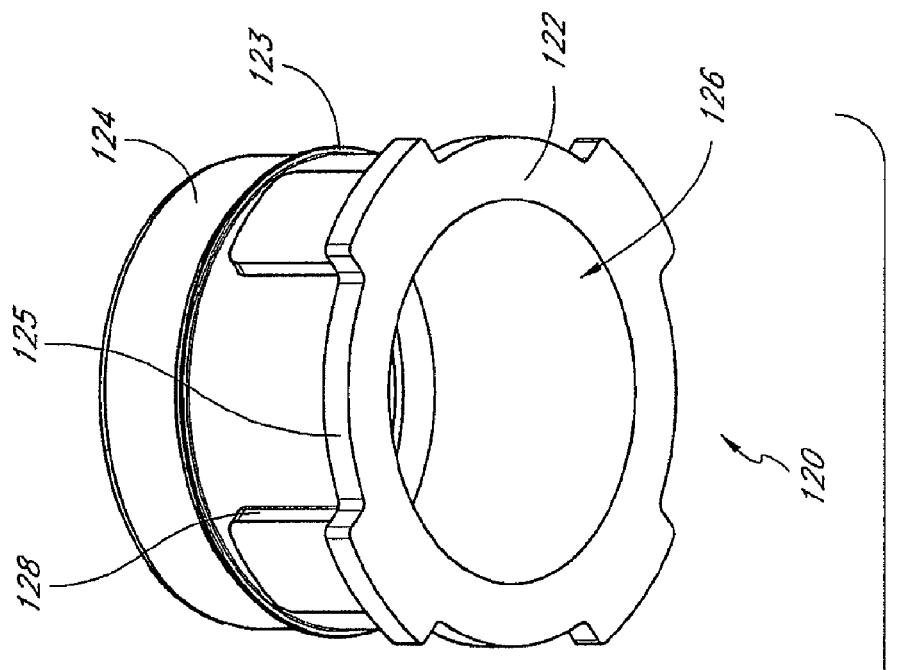
FIG. 3 schematically illustrates two perspective views of a thermal conduit compatible with certain embodiments described herein.
Figure 3:
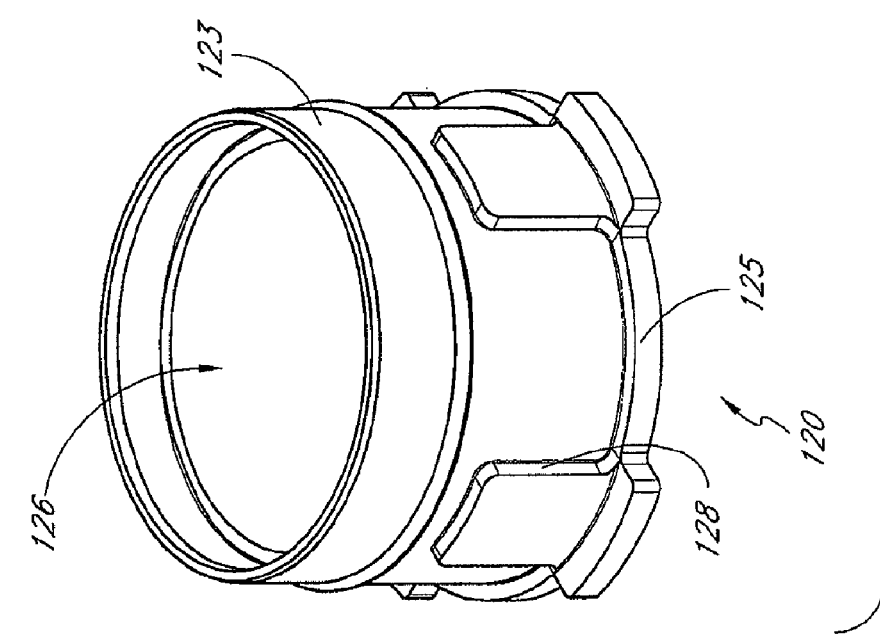

FIG. 3 schematically illustrates two perspective views of a thermal conduit 120 compatible with certain embodiments described herein. The thermal conduit 120 schematically illustrated by FIG. 3 comprises an elongate tube 123 having a first end portion 124 and a second end portion 125. The first end portion 124 is in thermal communication with the output optical element 120 and the second end portion 125 comprises the at least one surface 122 configured to be in thermal communication with the at least one heat dissipating surface 20 of the light delivery apparatus 10. The first end portion 124 of the thermal conduit 120 of certain embodiments comprises a hole 126 through which light from the light delivery apparatus 10 propagates to the output optical element 110 during operation. In certain embodiments, the output optical element 110 fits at least partially within the hole 126 and is in thermal communication with an inner surface of the first end portion 124. In certain other embodiments, the first end portion 124 comprises an outer surface which is in thermal communication with a portion of the output optical element 110.

Figure 4A:
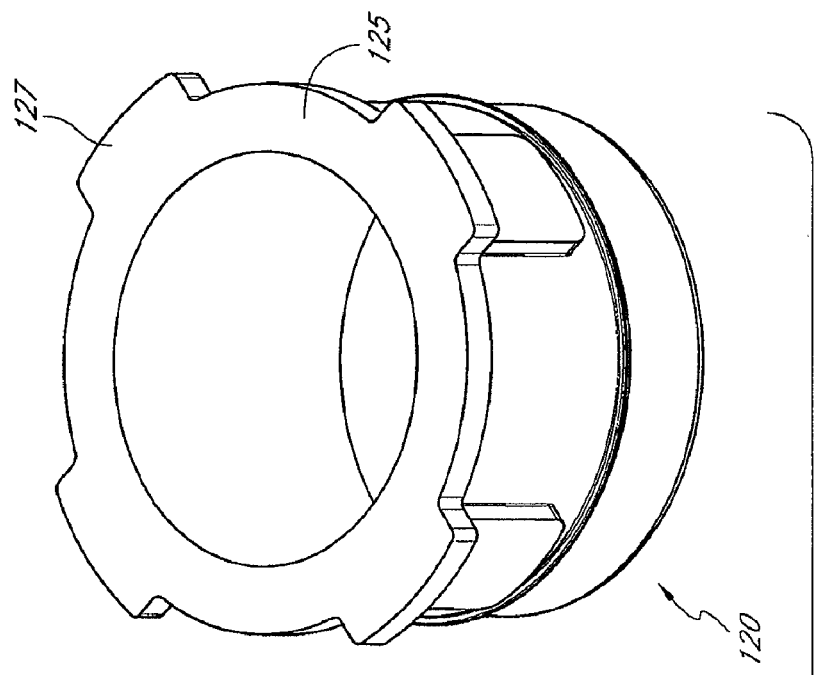
FIGS. 4A and 4B schematically illustrate example heat dissipating surfaces and example thermal conduits in accordance with certain embodiments described herein.
Figure 4A:
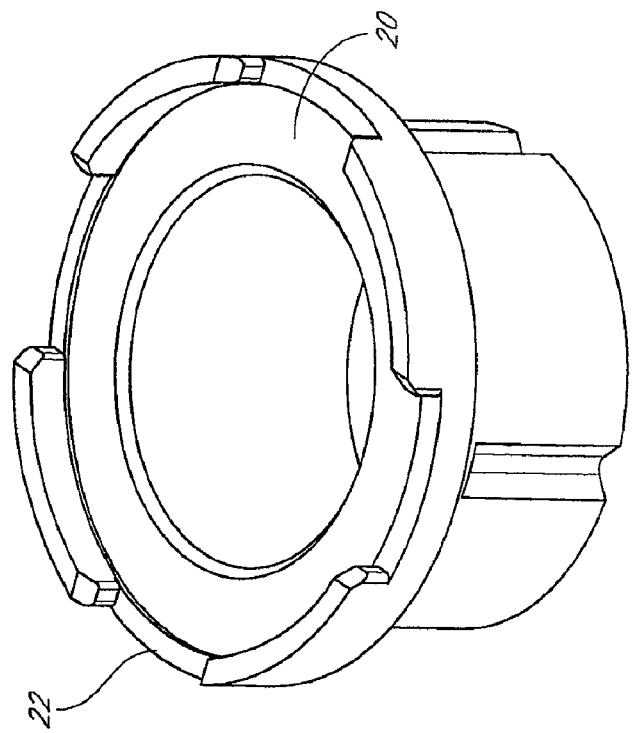
Figure 4B:
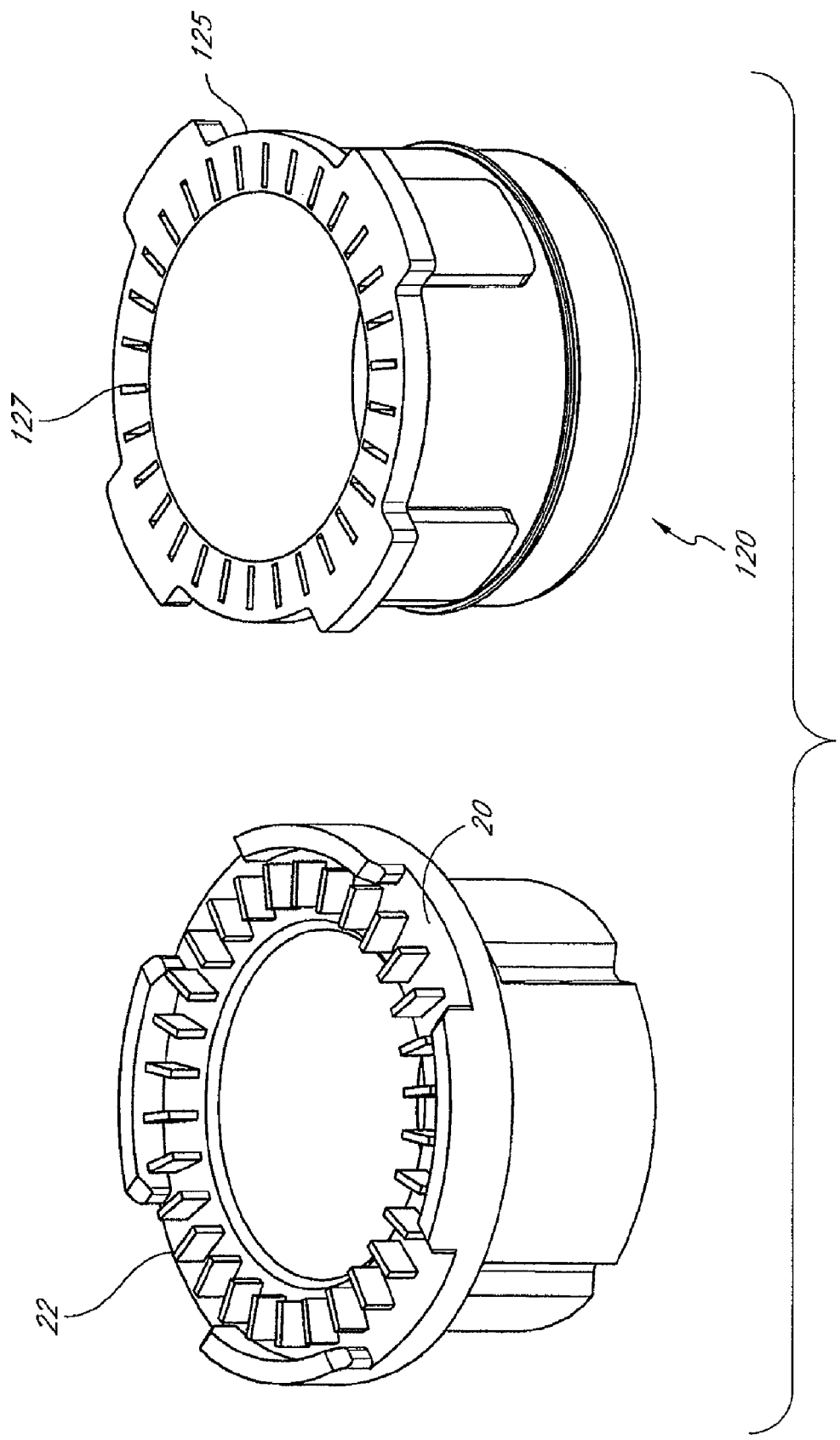

FIGS. 4A and 4B schematically illustrate example heat dissipating surfaces 20 and example thermal conduits 120 in accordance with certain embodiments described herein. In certain embodiments, the at least one surface 122 of the second end portion 125 comprises one or more portions 127 configured to fit with one or more portions 22 of the at least one heat dissipating surface 20. In certain embodiments, the one or more portions 127 and the one or more portions 22 provide registration of the second end portion 125 with the at least one heat dissipating surface 20. In certain embodiments, as schematically illustrated by FIG. 4A, the one or more portions 127 of the second end portion 125 comprise one or more protrusions and the one or more portions 22 of the at least one heat dissipating surface 20 comprise one or more recesses. For example, the protrusions can comprise substantially planar portions (e.g., four tabs) of the second end portion 125 and the recesses can comprise regions (e.g., four) between projections of the at least one heat dissipating surface 20 which extend substantially perpendicularly to the protrusions, as schematically illustrated by FIG. 4A.

In certain embodiments, the one or more portions 127 of the second end portion 125 comprise one or more recesses and the one or more portions 22 of the at least one heat dissipating surface 20 comprise one or more protrusions. For example, as schematically illustrated by FIG. 4B, the protrusions can comprise a plurality of fins or pins (e.g., more than ten) and the recesses can comprise slots or holes (e.g., more than ten) into which the fins at least partially fit. In certain embodiments, the fit of the protrusions into the recesses is sufficiently loose so that their relative alignment and the application force used to place the second end portion 125 of the thermal conduit 120 in thermal communication with the at least one heat dissipating surface 20 do not unduly hinder mounting the optical assembly 100 to the light delivery apparatus 10.

In certain embodiments, the one or more portions 127 of the second end portion 125 comprise one or more protrusions and recesses and the one or more portions 22 of the at least one heat dissipating surface 20 comprise one or more recesses and protrusions which are configured to fit with one or more portions 127 of the second end portion 125. Various other configurations of the heat dissipating surface 20 and the at least one surface 122 of the thermal conduit 120 are also compatible with certain embodiments described herein. In certain such embodiments, the numbers, shapes, sizes, and configurations of the one or more portions 127 can be selected to exhibit an appearance which is indicative of the manufacturer or source of the optical assembly 100.

Certain embodiments utilize a heat dissipating surface 20 and a thermal conduit 120 which advantageously control the allowable relative motion of the at least one surface 122 of the thermal conduit 120 and the at least one heat dissipating surface 20 of the light delivery apparatus 10 during the process of connecting and disconnecting the optical assembly 100 and the light delivery apparatus 10. For example, the at least one surface 122 can be restricted from rotating relative to the at least one heat dissipating surface 20 during the mounting or dismounting process so as to reduce any rubbing or friction between these two surfaces. Certain such embodiments in which the at least one surface 122 of the thermal conduit 120 does not rotate relative to the at least one heat dissipating surface 20 advantageously avoid wear of the at least one heat dissipating surface 20 due to repeated mounting/dismounting of optical assemblies 100. Rotation of the coupling portion 130 in certain embodiments engages the coupling portion 130 to the light delivery apparatus 10 without the output optical element 110 rotating relative to the light delivery apparatus 10.

In certain embodiments, at least one of the heat dissipating surface 20 of the light delivery apparatus 10 and the at least one surface 122 of the thermal conduit 120 comprises a material selected to improve the thermal conductivity between the at least one heat dissipating surface 20 and the at least one surface 122. For example, in certain embodiments, the at least one surface 122 can comprise a relatively soft material (e.g., indium plating) and the at least one heat dissipating surface 20 can comprise a relatively hard material (e.g., silicon carbide or diamond grit). In certain such embodiments, the hard material deforms the soft material at one or more contact points between the two surfaces, thereby making good thermal contact between the two surfaces.

In certain embodiments, an intervening material is placed between the at least one heat dissipating surface 20 and the at least one surface 122. In certain such embodiments, the intervening material advantageously improves the thermal conductivity between the at least one heat dissipating surface 20 and the at least one surface 122. For example, the intervening material can comprise a metal which is deformed by pressure between the at least one heat dissipating surface 20 and the at least one surface 122 or a thermally conductive grease.

In certain other embodiments, the intervening material is part of an adapter configured to be placed at least partially between the at least one heat dissipating surface 20 and the at least one surface 122. In certain embodiments, the adapter comprises one or more first portions (e.g., protrusions, recesses, or both) configured to fit with one or more portions (e.g., recesses, protrusions, or both) of the light delivery apparatus 10, and one or more second portions configured to fit with one or more portions of the thermal conduit 120. The adapter of certain embodiments can provide thermal conductivity between the at least one heat dissipating surface 20 and the thermal conduit 120. For example, the adapter of certain embodiments is configured to fit with the one or more portions 127 of the second end portion 125 and with the one or more portions 22 of the at least one heat dissipating surface 20. In certain such embodiments, the adapter is configured to fit with the one or more portions 127 and with the one or more portions 22 although the one or more portions 127 do not fit with the one or more portions 22. In this way, the adapter of certain embodiments advantageously provides a sufficient fit with the one or more portions 127 and with the one or more portions 22 so that an optical assembly 100 that would otherwise not mount to the light delivery apparatus 10 can be mounted to the light delivery apparatus 10.

The coupling portion 130 of certain embodiments is coupled to the thermal conduit 120, and provides a mechanism for attaching the thermal conduit 120 to the light delivery apparatus 10. In certain embodiments, the coupling portion 130 comprises one or more protrusions 132 configured to fit with one or more recesses of the light delivery apparatus 10. In certain embodiments, the coupling portion 130 comprises one or more recesses configured to fit with one or more protrusions of the light delivery apparatus 10.

Figure 5A:
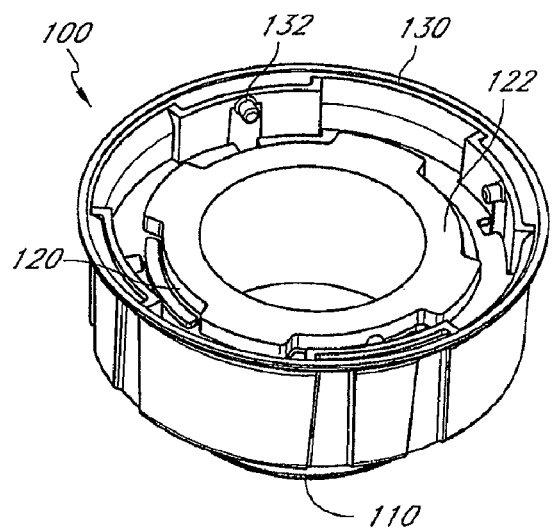
FIGS. 5A and 5B schematically illustrate two perspective views of an example optical assembly comprising a coupling portion in accordance with certain embodiments described herein.
Figure 5B:
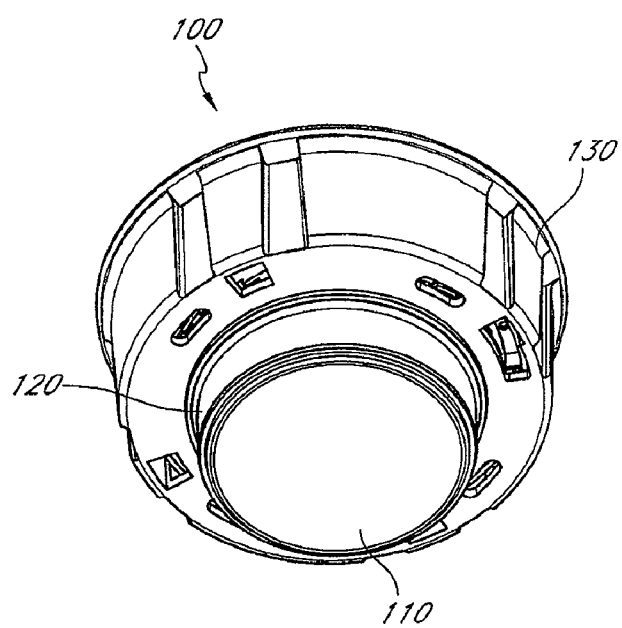
Figure 5C:
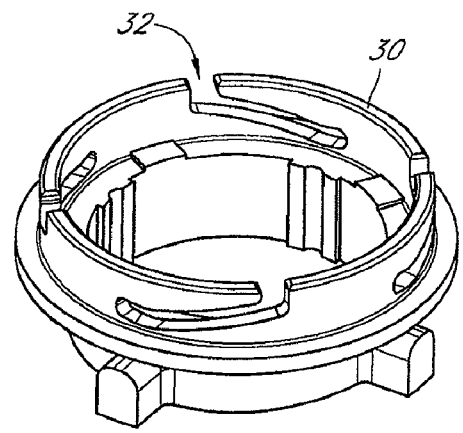
FIG. 5C schematically illustrates a perspective view of an example "bayonet ring" portion of the light delivery apparatus compatible with certain embodiments described herein.

FIGS. 5A and 5B schematically illustrate two perspective views of an example optical assembly 100 comprising a coupling portion 130 in accordance with certain embodiments described herein. FIG. 5C schematically illustrates a perspective view of an example "bayonet ring" portion 30 of the light delivery apparatus 10 compatible with certain embodiments described herein. In certain embodiments, the coupling portion 130 comprises one or more protrusions 132, as schematically illustrated by FIG. 5A, which are configured to fit with recesses 32 of a portion 30 of the light delivery apparatus 10, as schematically illustrated by FIG. 5C. In certain embodiments, the connection between the coupling portion 130 and the light delivery apparatus 10 is spring loaded (e.g., upon rotation of the optical assembly 100 relative to the light delivery apparatus 10 such that the protrusions 132 move along the recesses 32), such that upon connecting the optical assembly 100 to the light delivery apparatus 10, a force is generated which provides a consequent contact pressure between the at least one surface 125 of the thermal conduit 122 and the at least one heat dissipating surface 20 of the light delivery apparatus 10.

Figure 6C:
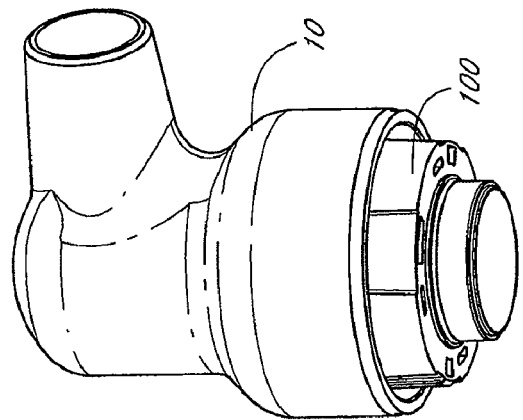
FIGS. 6A-6F schematically illustrate a series of configurations of the optical assembly and light delivery apparatus in accordance with certain embodiments described herein.
Figure 6B:
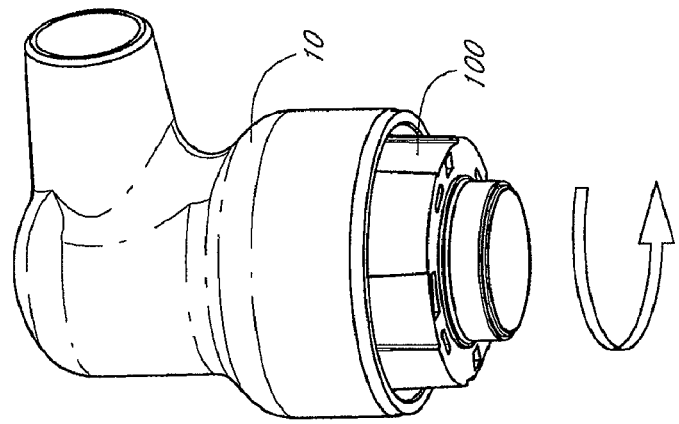
Figure 6A:
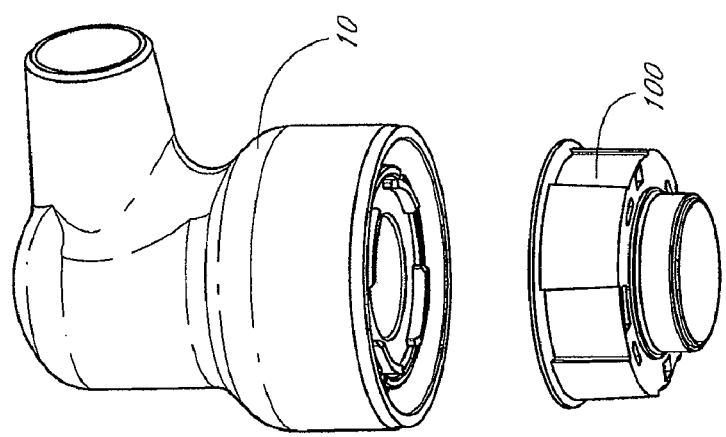

FIGS. 6A-6F schematically illustrate a series of configurations of the optical assembly 100 and light delivery apparatus 10 in accordance with certain embodiments described herein. FIGS. 6A-6C schematically illustrate an example process of placing the coupling portion 130 in the first state in which the coupling portion 130 is attached to the light delivery apparatus 10 such that the at least one surface 122 of the thermal conduit 120 is in thermal communication with the at least one heat dissipating surface 20 of the light delivery apparatus 10. In the configuration shown in FIG. 6A, the coupling portion 130 is in a third state in which the coupling portion 130 is unattached to the light delivery apparatus 10 and is configured to be attached to the light delivery apparatus 10 prior to being in the first state. In the configuration shown in FIG. 6B, the coupling portion 130 is placed in proximity to the light delivery apparatus 10, such that one or more portions of the coupling portion 130 at least partially engage with one or more portions of the light delivery apparatus 10. For example, as schematically illustrated by FIG. 6B, the optical assembly 100 is placed in contact with the light delivery apparatus 10 and the coupling portion 130 is rotated relative to the light delivery apparatus 10. In the configuration shown in FIG. 6C, the optical assembly 100 is attached to the light delivery apparatus 10 with the coupling portion 130 in the first state. In certain embodiments, the thermal conduit 120 is electrically coupled to an electrical ground when the coupling portion 130 is in the first state.

Figure 6F:
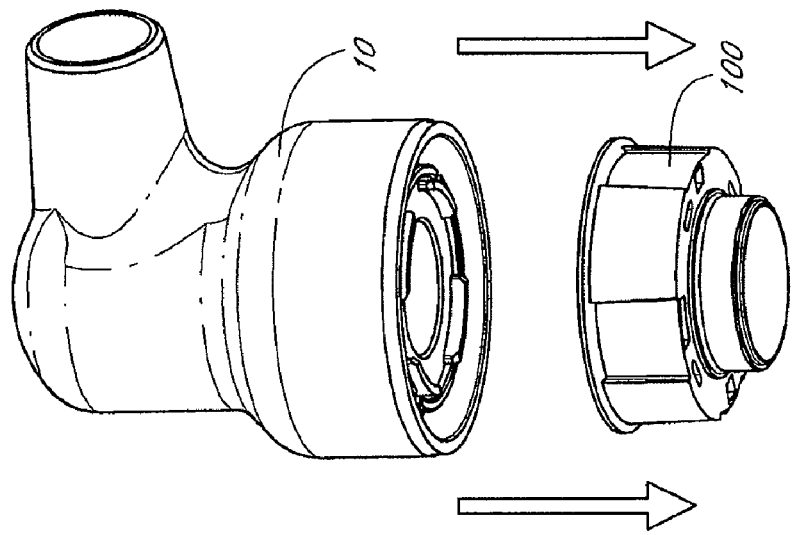
Figure 6E:
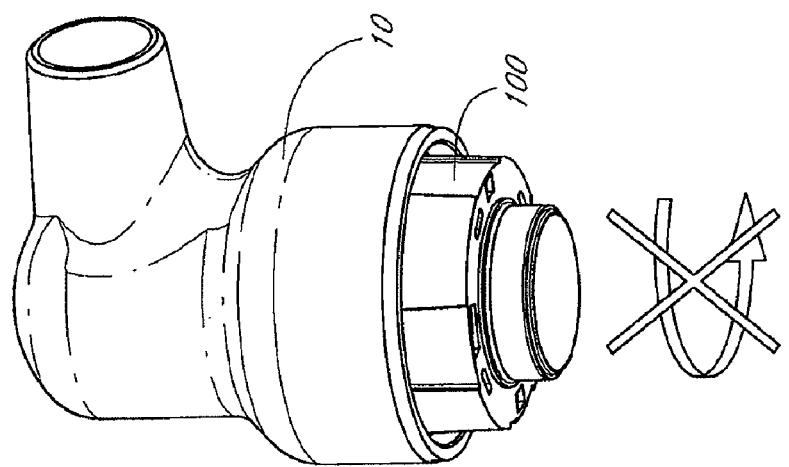
Figure 6D:
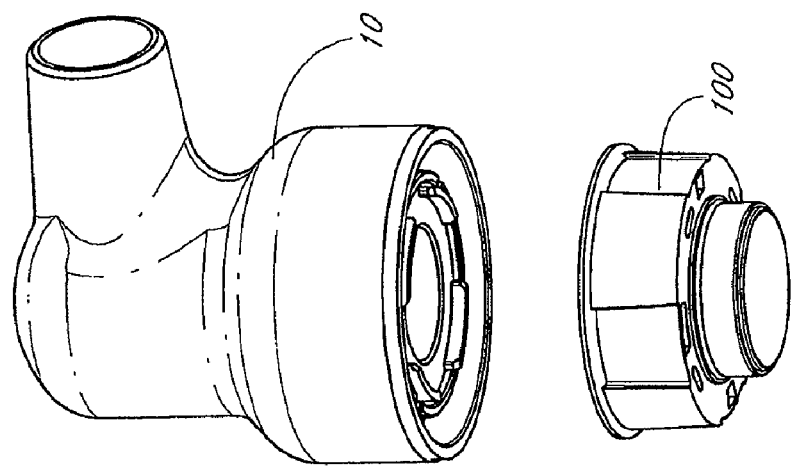

In certain embodiments, detaching the optical assembly 100 from the light delivery apparatus 10 after having been attached places the coupling portion 130 in the second state in which the coupling portion 130 is configured to prevent re-attachment of the coupling portion 130 to the light delivery apparatus 10. FIGS. 6D-6F schematically illustrate an example process of attempting to re-attach the optical assembly 100 to the light delivery apparatus 10 while the coupling portion 130 is in the second state. In the configuration shown in FIG. 6D, the coupling portion 130 is in the second state in which the coupling portion 130 is unattached to the light delivery apparatus 10 and is configured to prevent re-attachment to the light delivery apparatus 10 after being in the first state. In the configuration shown in FIG. 6D, the coupling portion 130 is placed in proximity to the light delivery apparatus 10 (e.g., the optical assembly 100 is placed in contact with the light delivery apparatus 10), but portions of the optical assembly 100 cannot engage portions of the light delivery apparatus 10 (e.g., even if the coupling portion 130 is attempted to be rotated relative to the light delivery apparatus 10, as schematically illustrated by FIG. 6E). In the configuration shown in FIG. 6F, the optical assembly 100 is not attached to the light delivery apparatus 10 and falls away from the light delivery apparatus 10.

Figure 7:
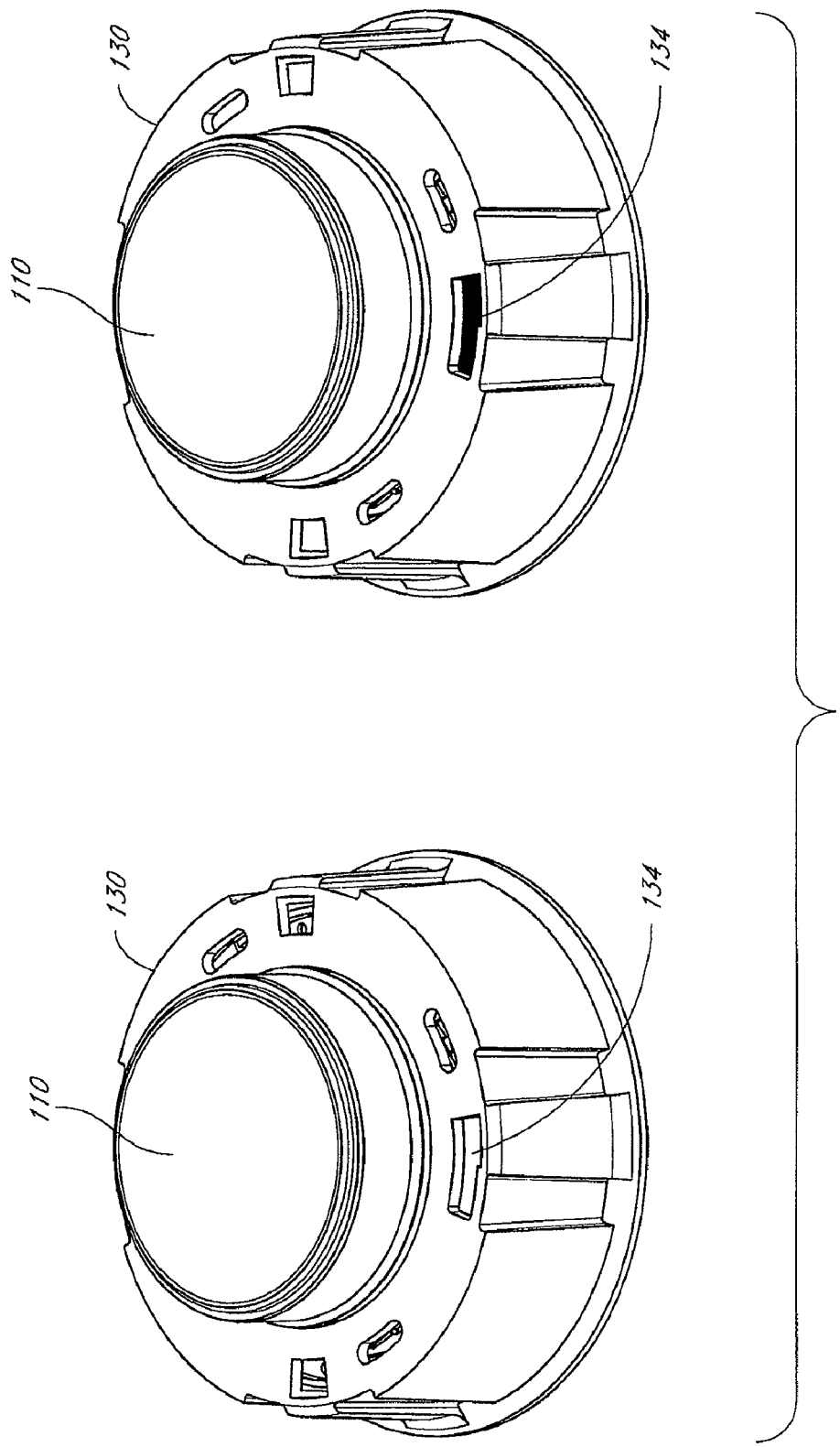
FIG. 7 schematically illustrates an example coupling portion comprising one or more indicators with two alternative appearances in accordance with certain embodiments described herein.

FIG. 7 schematically illustrates an example coupling portion 130 comprising one or more indicators 134 with two alternative appearances in accordance with certain embodiments described herein. In certain embodiments, the indicator 134 provides a visual indication of the current state in which the coupling portion 130 is in. For example, on the left side of FIG. 7, the indicator 134 displays a first color (e.g., green) indicative of the coupling portion 130 being in the first state. On the right side of FIG. 7, the indicator 134 displays a second color (e.g., red) indicative of the coupling portion 130 being in the second state. Certain other embodiments utilize an indicator 134 located at other positions of the coupling portion 130. Certain other embodiments utilize one or more indicators 134 with other indicia of the state of the coupling portion 130, including but not limited to, alphanumeric characters.

In certain embodiments, the coupling portion 130 comprises a mechanism 140 which allows rotation of the coupling portion 130 in a first direction to place the coupling portion 130 in the first state and which allows rotation of the coupling portion 130 in a second direction opposite to the first direction to remove the coupling assembly 130 from the first state. The mechanism 140 of certain such embodiments is configured to inhibit rotation of the coupling portion 130 in the first direction upon the coupling portion 130 being removed from the first state.

Figure 8:
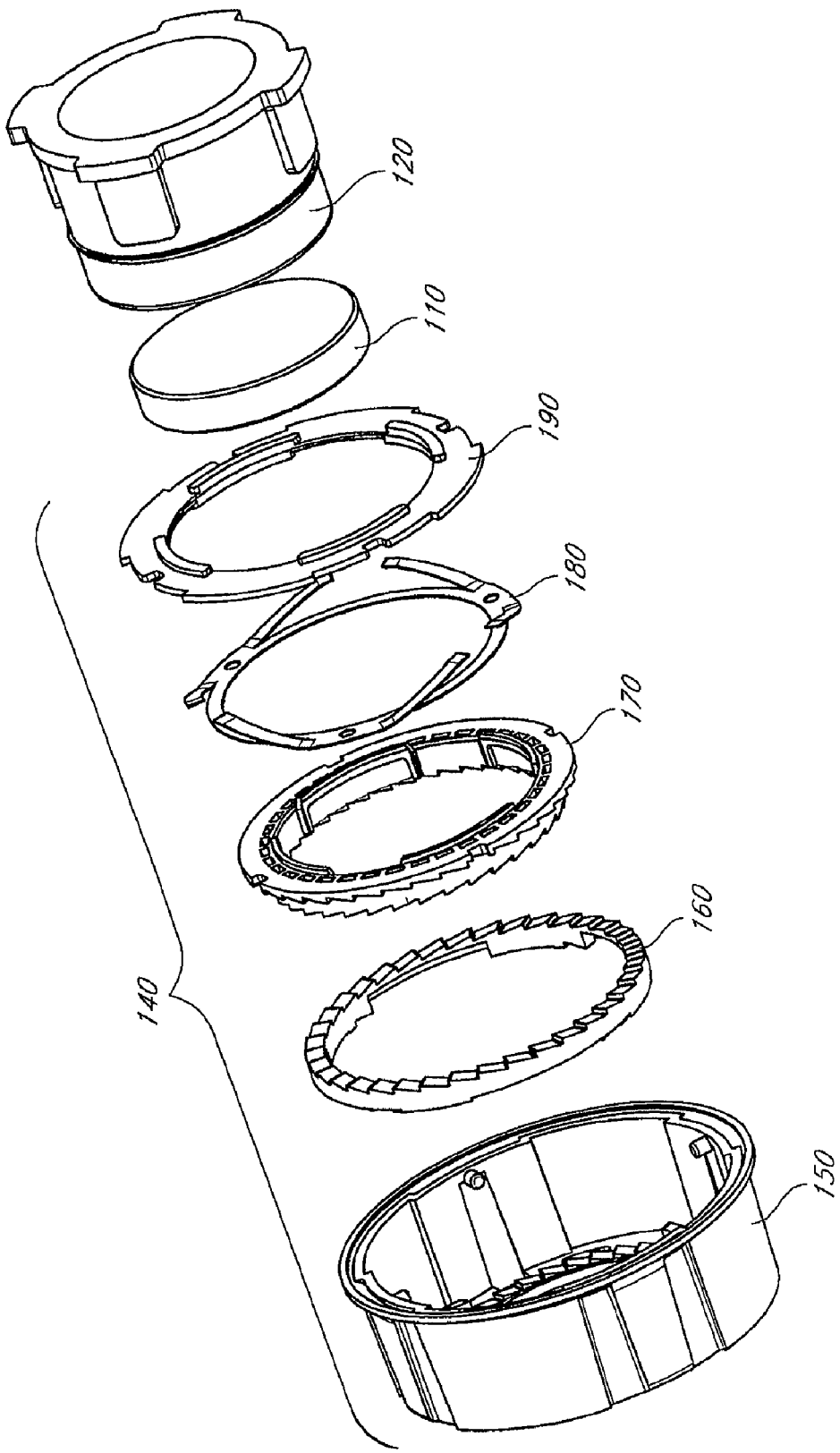
FIG. 8 schematically illustrates an exploded perspective view of an example mechanism in accordance with certain embodiments described herein.

FIG. 8 schematically illustrates an exploded perspective view of an example mechanism 140 in accordance with certain embodiments described herein. In certain embodiments, the mechanism 140 comprises a first element 150, a second element 160, and a third element 170. In certain embodiments, the second element 160 is between the first element 150 and the third element 170.

Figure 9:
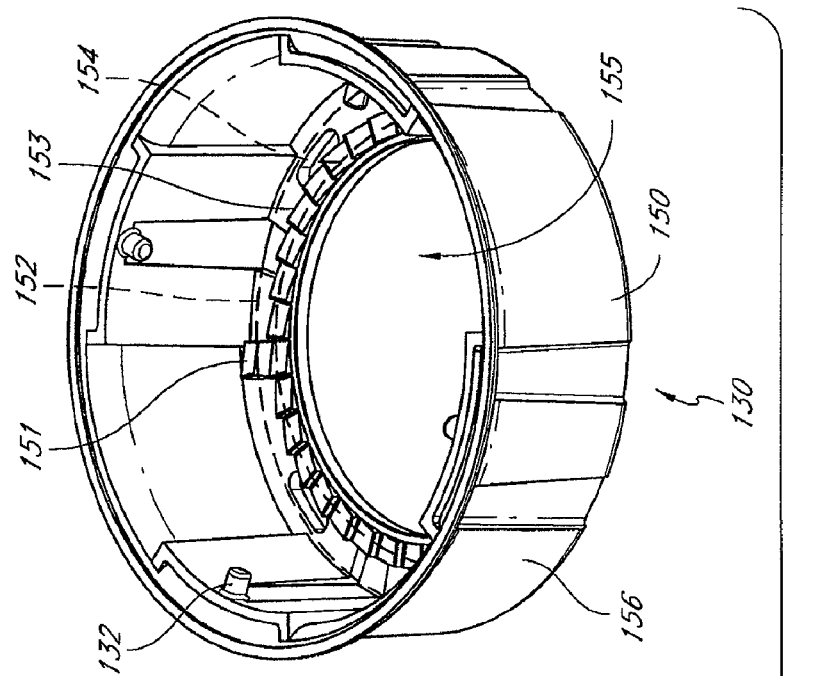
FIG. 9 schematically illustrates two perspective views of an example first element in accordance with certain embodiments described herein.
Figure 9:
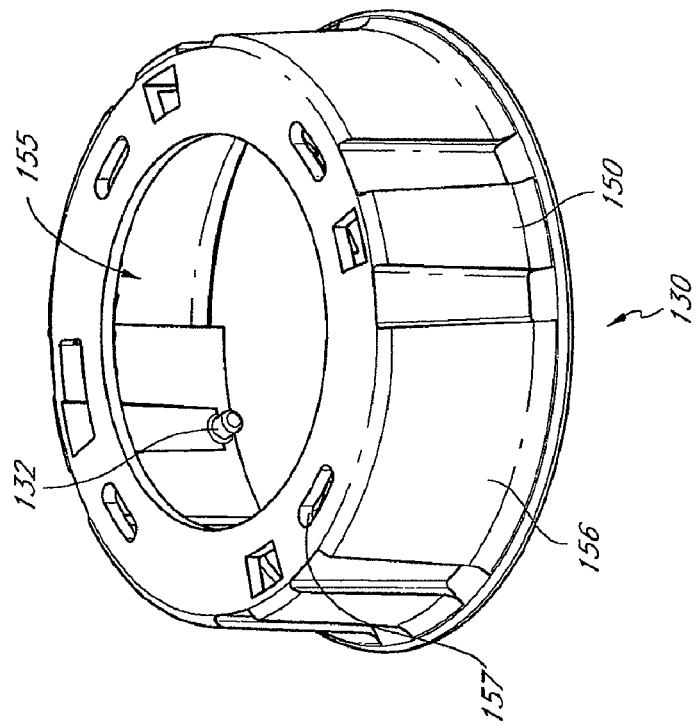

FIG. 9 schematically illustrates two perspective views of an example first element 150 in accordance with certain embodiments described herein. In certain embodiments, the first element 150 comprises a plastic resin (e.g., thermoplastic polymer, acrylonitrile butadiene styrene or ABS, polyvinyl chloride or PVC, acetal-based), although other materials are also compatible with certain embodiments described herein. In certain embodiments, the first element 150 is a portion of the coupling portion 130, as schematically illustrated by FIG. 9. The first element 150 comprises a first plurality of protrusions 151 (e.g., ratchet teeth) positioned along a first circle 152 and a second plurality of protrusions 153 (e.g., ratchet teeth) positioned along a second circle 154 substantially concentric with the first circle 152. The first element 150 of certain embodiments has a generally cylindrical shape. In certain embodiments, the protrusions 151 and the protrusions 153 are on an inner surface of the first element 150. In certain embodiments, the protrusions 151 extend further from the inner surface than do the protrusions 153. In certain embodiments, the first plurality of protrusions 151 have a smaller number of protrusions (e.g., four) than does the second plurality of protrusions 153 (e.g., between 20 and 40).

The first element 150 of certain embodiments further comprises a hole 155 generally concentric with the first circle 152 and the second circle 154 through which the thermal conduit 120 is configured to extend. The first element 150 of certain embodiments further comprises an outer housing 156 configured to be gripped by a user to attach/detach the coupling portion 130 to/from the light delivery apparatus 10. In certain embodiments, the first element 150 further comprises the protrusions 132 (e.g., pins extending radially inward towards a center of the first element 150) of the coupling portion 130 which fit in respective recesses of the light delivery apparatus 10. In certain such embodiments, the first element 150 is configured to be removably affixed to the light delivery apparatus 10 thereby allowing the coupling portion 130 to be attached and detached from the light delivery apparatus 10. In certain embodiments, the first element 150 further comprises one or more indicator holes 157 through which a user can see the one or more indicators 134 of the coupling portion 130.

Figure 10:
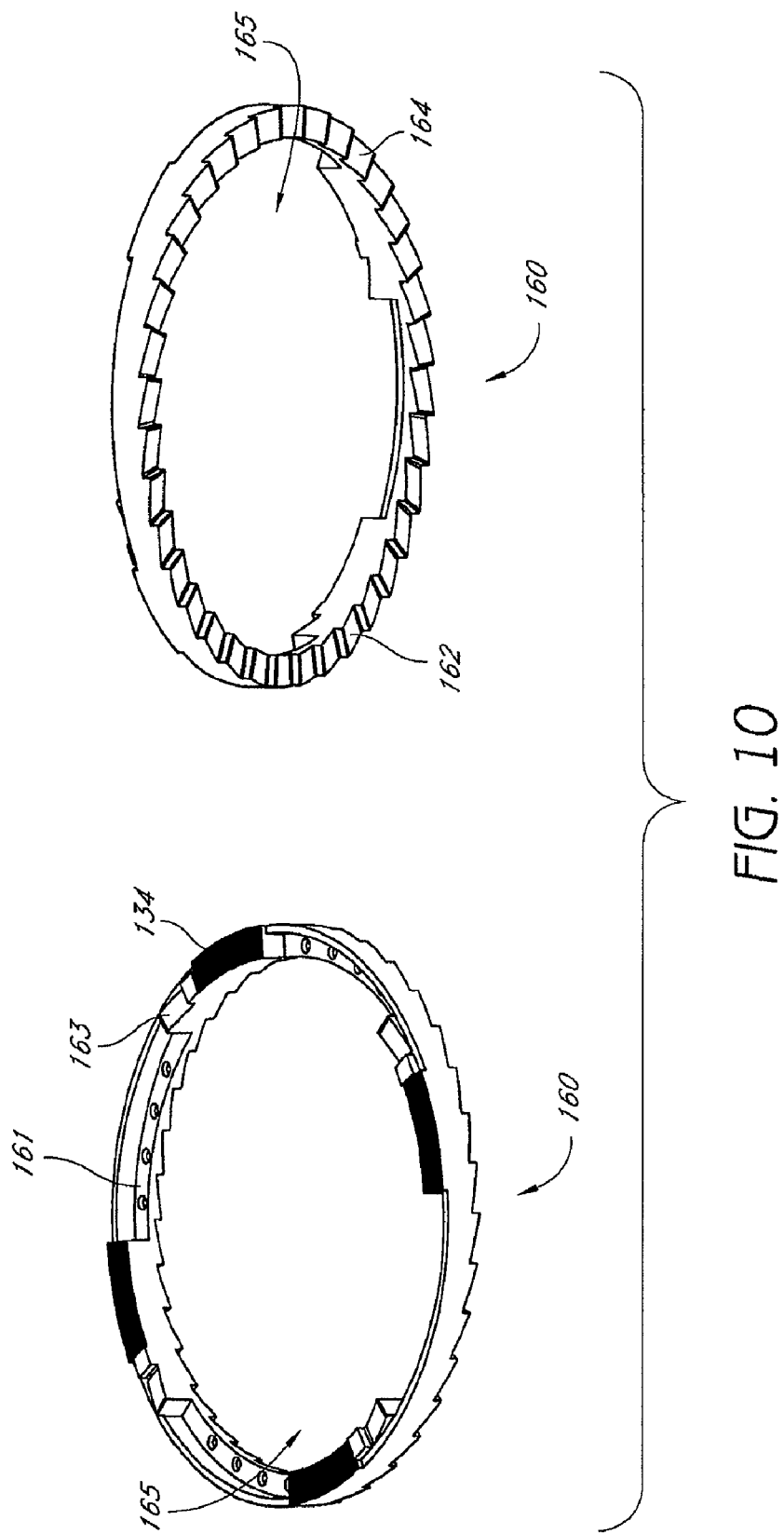
FIG. 10 schematically illustrates two perspective views of an example second element in accordance with certain embodiments described herein.

FIG. 10 schematically illustrates two perspective views of an example second element 160 in accordance with certain embodiments described herein. In certain embodiments, the second element 160 comprises a plastic resin (e.g., thermoplastic polymer, acrylonitrile butadiene styrene or ABS, polyvinyl chloride or PVC, acetal-based), although other materials are also compatible with certain embodiments described herein. The second element 160 comprises a first side 161 and a second side 162 opposite to the first side 161. The second element 160 further comprises a third plurality of protrusions 163 (e.g., ratchet teeth) on the first side 161 and configured to mate with the first plurality of protrusions 151. The second element 160 further comprises a fourth plurality of protrusions 164 (e.g., ratchet teeth) on the second side 162. In certain embodiments, the second element 160 is generally annular with a hole 165 through which the thermal conduit 120 is configured to extend. In certain embodiments, the third plurality of protrusions 163 have a smaller number of protrusions (e.g., four) than does the fourth plurality of protrusions 164 (e.g., between 20 and 40). In certain embodiments, the first side 161 further comprises the one or more indicators 134 of the coupling portion 130.

Figure 11:
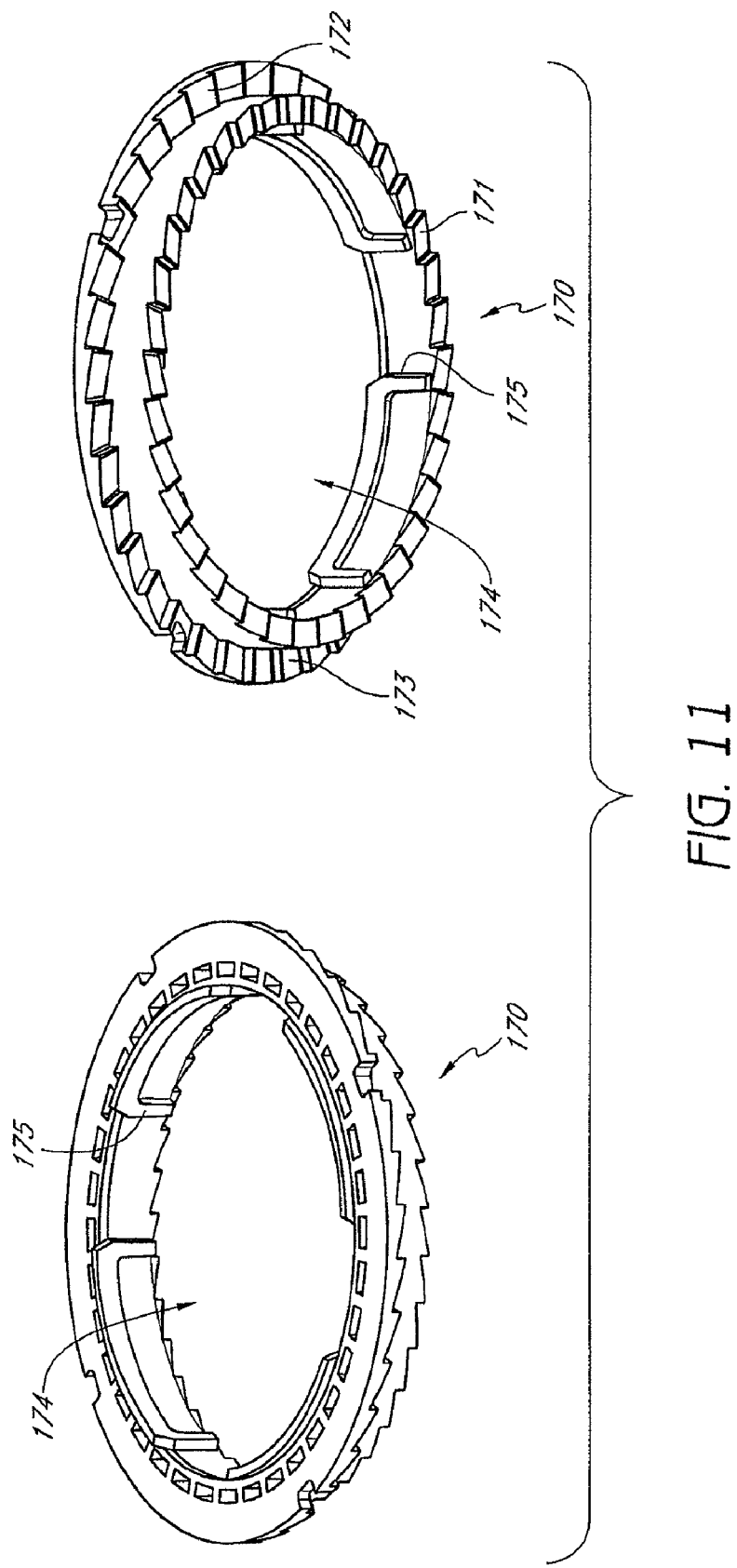
FIG. 11 schematically illustrates two perspective views of an example third element in accordance with certain embodiments described herein.

FIG. 11 schematically illustrates two perspective views of an example third element 170 in accordance with certain embodiments described herein. In certain embodiments, the third element 170 comprises a plastic resin (e.g., thermoplastic polymer, acrylonitrile butadiene styrene or ABS, polyvinyl chloride or PVC, acetal-based), although other materials are also compatible with certain embodiments described herein. The third element 170 comprises a fifth plurality of protrusions 171 (e.g., ratchet teeth) configured to mate with the second plurality of protrusions 153. The third element 170 further comprises a sixth plurality of protrusions 172 (e.g., ratchet teeth) configured to mate with the fourth plurality of protrusions 164. The fifth plurality of protrusions 171 and the sixth plurality of protrusions 172 of certain embodiments are on the same side 173 of the third element 170 but with the protrusions 171 extending farther from the side 173 than do the protrusions 172, as schematically illustrated by FIG. 11. In certain embodiments, the fifth plurality of protrusions 171 extend through the hole 165 of the second element 160 to engage the second plurality of protrusions 153 of the first element 150. In certain embodiments, the third element 170 is generally annular with a hole 174 through which the thermal conduit 120 is configured to extend. In certain embodiments, the third element 170 further comprises one or more portions 175 which engage corresponding portions 128 of the thermal conduit 120, such that the third element 170 is keyed to the thermal conduit 120.

Figure 12:
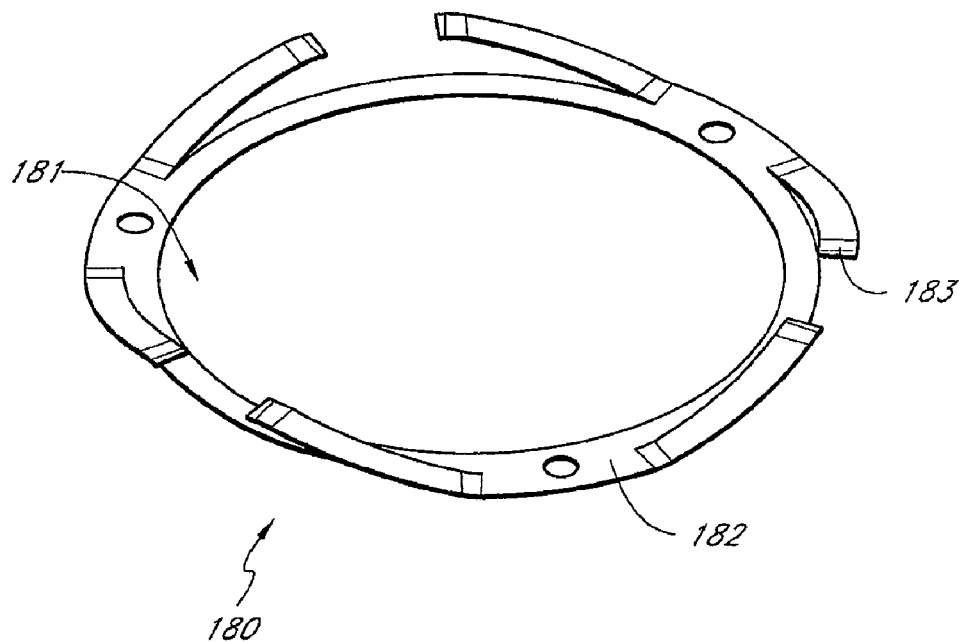
FIG. 12 schematically illustrates an example spring element in accordance with certain embodiments described herein.

In certain embodiments, the mechanism 140 further comprises a spring element 180 and a plate element 190, as schematically illustrated in FIG. 8. FIG. 12 schematically illustrates an example spring element 180 in accordance with certain embodiments described herein. In certain embodiments, the spring element 180 comprises a metal (e.g., stainless steel), although other materials are also compatible with certain embodiments described herein. The spring element 180 of certain embodiments is generally annular with a hole 181 through which the thermal conduit 120 is configured to extend. The spring element 180 of certain embodiments has a portion 182 configured to press against the third element 170 (e.g., against a side opposite to the side 173). In certain embodiments, the spring element 180 comprises one or more leaf springs 183 which extend away from the portion 182, as schematically illustrated by FIG. 12. As described more fully below, the spring element 180 is placed between the third element 170 and the plate element 190, such that the leaf springs 183 are compressed thereby providing a force on the third element 170 towards the second element 160 and the first element 150.

Figure 13:
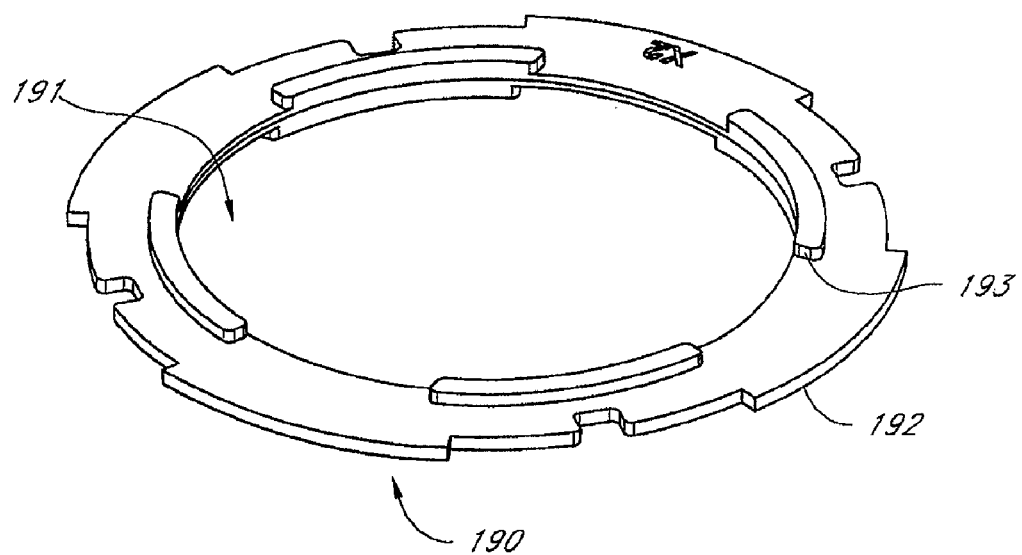
FIG. 13 schematically illustrates an example plate element in accordance with certain embodiments described herein.

FIG. 13 schematically illustrates an example plate element 190 in accordance with certain embodiments described herein. In certain embodiments, the plate element 190 comprises a plastic resin (e.g., thermoplastic polymer, acrylonitrile butadiene styrene or ABS, polyvinyl chloride or PVC, acetal-based), although other materials are also compatible with certain embodiments described herein. The plate element 190 of certain embodiments is generally annular with a hole 191 through which the thermal conduit 120 is configured to extend. In certain embodiments, the plate element 190 comprises one or more portions 192 configured to engage one or more portions of the first element 150. In certain embodiments, the plate element 190 further comprises one or more portions 193 configured to engage one or more portions (e.g., portions 127) of the thermal conduit 120.

Figure 14A:
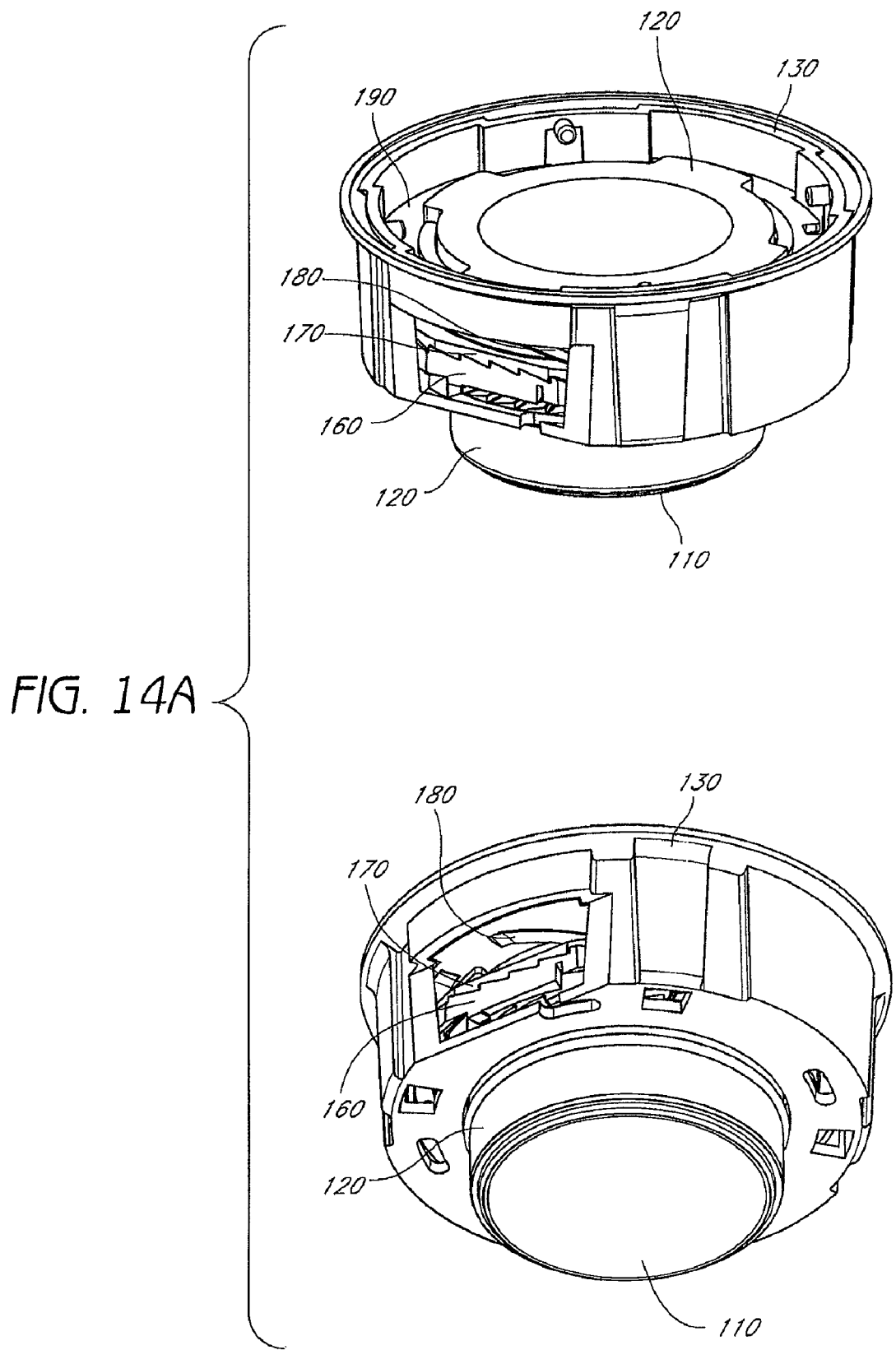
FIG. 14A schematically illustrates two perspective views of an example optical assembly in accordance with certain embodiments described herein with the first element partially cut-away.

FIG. 14A schematically illustrates two perspective views of an example optical assembly 100 in accordance with certain embodiments described herein with the first element 150 partially cut-away. FIG. 14B schematically illustrates two perspective views of the example optical assembly 100 of FIG. 14A with the first element 150 totally removed. In certain embodiments, to mount the optical assembly 100 to the light delivery apparatus 10, the optical assembly 100 is placed in proximity to the light delivery apparatus 10. For example, the optical assembly 100 is at least partially inserted into the light delivery apparatus 10 such that the portions 127 of the thermal conduit 120 mate with the portions 22 of the at least one heat dissipating surface 20 of the light delivery apparatus 10. In this position, the protrusions 132 of the coupling portion 130 are inserted into the recesses 32 of the portion 30 of the light delivery apparatus 10. In certain embodiments, the coupling portion 130 is rotated (e.g., clockwise) relative to the light delivery apparatus 10, while the thermal conduit 120 does not rotate relative to the at least one heat dissipating surface 20. This rotation pulls the coupling portion 130 and the portion of the light delivery apparatus 10 towards one another, and also pulls the thermal conduit 120 and the at least one heat dissipating surface 130 towards one another, and creates a thermal contact force pressing the thermal conduit 120 and at least one heat dissipating surface 130 together.

Before the coupling portion 130 is in the first state, the third element 170 is disengaged from the first element 150. During the rotation of the coupling portion 130, the second element 160 rotates with the first element 150 (which is part of the coupling portion 130), driven by the first plurality of protrusions 151 of the first element 150. This action causes the third element 170 (which is keyed to the thermal conduit 120) to ratchet up and down as the fourth plurality of protrusions 164 pass beneath the sixth plurality of protrusions 172. Rotation of the coupling portion 130 stops in certain embodiments when the protrusions 132 of the coupling portion 130 reach the ends of the recesses 32 of the portion 30 of the light delivery apparatus 10. In this position, the optical assembly 100 is mounted to the light delivery apparatus 10 and is positioned for operation of the light delivery apparatus 10. In certain embodiments, one or more portions (e.g., green portions) of the first side 161 of the second element 160 align with the one or more indicator windows 157 of the first element 150 to indicate that the coupling portion 130 is in the first state.

In certain embodiments, to detach the optical assembly 100 from the light delivery apparatus 10, the coupling portion 130 is rotated in the opposite direction (e.g., counterclockwise) relative to the light delivery apparatus 10. During this rotation, the second element 160 is prevented from rotating by the interaction of the fourth plurality of protrusions 164 with the sixth plurality of protrusions 172. Once the coupling portion 130 of certain embodiments has been rotated by a predetermined angle (e.g., 10 degrees), the second element 160 disengages (e.g., moves off) from the first plurality of protrusions 151 of the first element 150. This action forces the third element 170 to move as well, allowing the fifth plurality of protrusions 171 to engage with the second plurality of protrusions 153 of the first element 150, such that the third element 170 is engaged with the first element 150 when the coupling portion 130 is in the second state. This interaction of the protrusions 171 and protrusions 153 prevents subsequent rotations of the coupling portion 130 in the direction (e.g., clockwise) for mounting the optical assembly 100 on the light delivery apparatus 10.

Counter-clockwise rotation of the coupling portion 130 can continue in certain embodiments until the protrusions 132 reach the end of the recesses 32 of the portion 30 of the light delivery apparatus 10, upon which the coupling portion 130 can be pulled away from the light delivery apparatus 10. In certain embodiments, one or more portions (e.g., red portions) of the first side 161 of the second element 160 align with the one or more indicator windows 157 of the first element 150 to indicate that the coupling portion 130 is in the second state.

Figure 15:
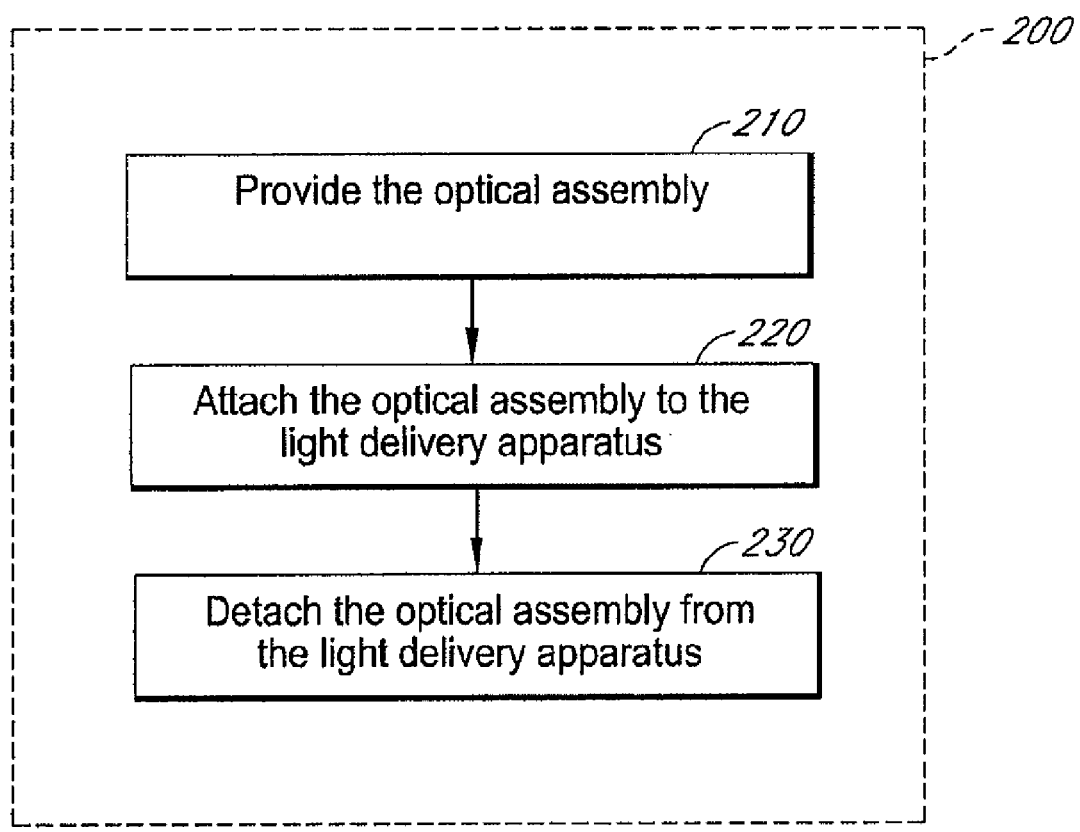
FIG. 15 is a flow diagram of an example method of releasably mounting an optical assembly to a light delivery apparatus in accordance with certain embodiments described herein.

FIG. 15 is a flow diagram of an example method 200 of releasably mounting an optical assembly 100 to a light delivery apparatus 10 in accordance with certain embodiments described herein. In an operational block 210, the method 200 comprises providing the optical assembly 100. The optical assembly 100 is adapted to be in at least two states comprising a first state and a second state. In the first state, the optical assembly 100 is attached to the light delivery apparatus 10. In the second state, the optical assembly 100 is detached from the light delivery apparatus 10 after having been attached to the light delivery apparatus 10 in the first state. Also, in the second state, the optical assembly 100 is configured to prevent re-attachment of the optical assembly 100 to the light delivery apparatus 10. In an operational block 220, the method 200 further comprises attaching the optical assembly 100 to the light delivery apparatus 10. In an operational block 230, the method 200 further comprises detaching the optical assembly 100 from the light delivery apparatus 10.

In certain embodiments, the light delivery apparatus 10 comprises a mounting portion 30 and at least one heat dissipating surface 20, and the optical assembly 100 comprises a coupling portion 130 and at least one surface 122 of a thermal conduit 120. Attaching the optical assembly 100 to the light delivery apparatus 10 in certain such embodiments comprises rotating the coupling portion 130 relative to the mounting portion 30 without the at least one surface 122 of the thermal conduit 120 rotating relative to the at least one heat dissipating surface 20.

In certain embodiments, attaching the optical assembly 100 to the light delivery apparatus 10 places the optical assembly 100 in the first state and detaching the optical assembly 100 from the light delivery apparatus 10 places the optical assembly 100 in the second state. In certain embodiments, a user of the optical assembly 100 and the light delivery apparatus 10 may seek to override the single-use functionality of the optical assembly 100. For example, in certain embodiments, the user may utilize an adapter between the optical assembly 100 and the light delivery apparatus 10. Such an adapter would be configured to mate to the light delivery apparatus 10 and to mate with the optical assembly 100. In certain such embodiments, the adapter would be configured to mate with the optical assembly 100 when the optical assembly 100 is in the first state, when the optical assembly 100 is in the second state, or when the optical assembly 100 is in either the first state or the second state. In certain other embodiments, the adapter would be configured so that the optical assembly 100 is not placed in the second state when the optical assembly 100 is detached from the adapter. Thus, detaching the optical assembly 100 from the light delivery apparatus 10 in certain such embodiments comprises avoiding placing the optical assembly 100 in the second state.

Various embodiments have been described above. Although this invention has been described with reference to these specific embodiments, the descriptions are intended to be illustrative of the invention and are not intended to be limiting. Various modifications and applications may occur to those skilled in the art without departing from the true spirit and scope of the invention as defined in the appended claims.

What is claimed is:

1. An optical assembly attachable to and detachable from a light delivery apparatus, the optical assembly comprising:
    a thermally conductive and optically transmissive element; and
    a thermal conduit in thermal communication with the element and comprising at least one surface configured to be in thermal communication with at least one heat dissipating surface of the light delivery apparatus;
    wherein the optical assembly is configured to be attached to the light delivery apparatus such that the at least one surface of the thermal conduit is in thermal communication with the at least one heat dissipating surface, and is configured to prevent re-attachment of the optical assembly to the light delivery apparatus upon being detached from the light delivery apparatus after having been attached to the light delivery apparatus.

2. The optical assembly of claim 1, wherein the element comprises sapphire.

3. The optical assembly of claim 1, wherein the thermal conduit comprises an elongate tube having a first end portion in thermal communication with the element and a second end portion comprising the at least one surface.

4. The optical assembly of claim 1, wherein the thermal conduit comprises a hole through which light from the light delivery apparatus propagates to the element.

5. The optical assembly of claim 1, wherein the thermal conduit is electrically coupled to an electrical ground when the optical assembly is attached to the light delivery apparatus.

6. The optical assembly of claim 1, further comprising an adapter configured to fit with the light delivery apparatus, wherein the adapter provides thermal conductivity between the at least one heat dissipating surface and the thermal conduit.

7. The optical assembly of claim 1, wherein the coupling portion comprises an indicator configured to indicate a current state of the optical assembly.

8. The optical assembly of claim 1, further comprising a mechanism that rotates in a first direction to attach the optical assembly to the light delivery apparatus and that rotates in a second direction opposite to the first direction to detach the optical assembly from the light delivery apparatus, the mechanism configured to be prevented from rotation in the first direction upon the optical assembly being detached from the light delivery assembly.

9. An optical assembly releasably mountable to a light delivery apparatus comprising at least one heat dissipating surface, the optical assembly comprising:
   an optical element comprising a thermally conductive and optically transmissive material;
   a thermal conduit in thermal communication with the output optical element and comprising at least one surface configured to be in thermal communication with the at least one heat dissipating surface; and
   a coupling portion configured to releasably mount to the light delivery apparatus such that the at least one surface of the thermal conduit is in thermal communication with the at least one heat dissipating surface by rotating relative to and engaging a corresponding portion of the optical assembly without the at least one surface of the thermal conduit rotating relative to the at least one heat dissipating surface.

10. The optical assembly of claim 9, wherein rotation of the coupling portion engages the coupling portion to the light delivery apparatus without the output optical element rotating relative to the light delivery apparatus.

11. A method of using an optical assembly, the method comprising:
   providing an optical assembly comprising a thermally conductive and optically transmissive element and a thermal conduit in thermal communication with the element and comprising at least one surface configured to be in thermal communication with at least one heat dissipating surface of the light delivery apparatus;
   attaching the optical assembly to the light delivery apparatus such that the at least one surface of the thermal conduit is in thermal communication with the at least one heat dissipating surface; and
   detaching the optical assembly from the light delivery apparatus such that the optical assembly is prevented from re-attachment to the light delivery apparatus.

12. The method of claim 11, wherein the light delivery apparatus comprises a mounting portion and the optical assembly comprises a coupling portion, wherein attaching the optical assembly to the light delivery apparatus comprises rotating the coupling portion relative to the mounting portion without the at least one surface of the thermal conduit rotating relative to the at least one heat dissipating surface.

13. The method of claim 11, wherein the element comprises sapphire.

14. The method of claim 11, wherein the thermal conduit comprises an elongate tube having a first end portion in thermal communication with the element and a second end portion comprising the at least one surface.

15. The method of claim 11, wherein the thermal conduit comprises a hole through which light from the light delivery apparatus propagates to the element.

16. The method of claim 11, wherein attaching the optical assembly comprises electrically coupling the thermal conduit to an electrical ground.

* * * * *